(12) United States Patent
Videbaek

(10) Patent No.: US 8,485,989 B2
(45) Date of Patent: Jul. 16, 2013

(54) BIOPSY APPARATUS HAVING A TISSUE SAMPLE RETRIEVAL MECHANISM

(75) Inventor: Karsten Videbaek, Jyllinge (DK)

(73) Assignee: Bard Peripheral Vascular, Inc., Tempe, AZ (US)

( * ) Notice: Subject to any disclaimer, the term of this patent is extended or adjusted under 35 U.S.C. 154(b) by 409 days.

(21) Appl. No.: 12/551,819

(22) Filed: Sep. 1, 2009

(65) Prior Publication Data
US 2011/0054350 A1    Mar. 3, 2011

(51) Int. Cl.
*A61B 10/02* (2006.01)

(52) U.S. Cl.
USPC ............ 600/568; 600/566; 600/567; 600/575

(58) Field of Classification Search
USPC ........................................ 600/566–568, 575
See application file for complete search history.

(56) References Cited

U.S. PATENT DOCUMENTS

| | | |
|---|---|---|
| 737,293 A | 8/1903 | Summerfeldt |
| 1,585,934 A | 5/1926 | Muir |
| 1,663,761 A | 3/1928 | Johnson |
| 2,953,934 A | 9/1960 | Sundt |
| 3,019,733 A | 2/1962 | Braid |
| 3,224,434 A | 12/1965 | Molomut et al. |
| 3,477,423 A | 11/1969 | Griffith |
| 3,512,519 A | 5/1970 | Hall |
| 3,561,429 A | 2/1971 | Jewett et al. |
| 3,565,074 A | 2/1971 | Foti |
| 3,606,878 A | 9/1971 | Kellogg |
| 3,727,602 A | 4/1973 | Hyden et al. |
| 3,732,858 A | 5/1973 | Banko |
| 3,800,783 A | 4/1974 | Jamshidi |
| 3,844,272 A | 10/1974 | Banko |
| 3,882,849 A | 5/1975 | Jamshidi |
| 4,275,730 A | 6/1981 | Hussein |
| 4,282,884 A | 8/1981 | Boebel |
| 4,306,570 A | 12/1981 | Matthews |
| 4,354,092 A | 10/1982 | Manabe et al. |
| 4,445,509 A | 5/1984 | Auth |
| 4,490,137 A | 12/1984 | Moukheibir |
| 4,549,554 A | 10/1985 | Markham |
| 4,577,629 A | 3/1986 | Martinez |
| 4,589,414 A | 5/1986 | Yoshida et al. |
| 4,603,694 A | 8/1986 | Wheeler |
| 4,605,011 A | 8/1986 | Naslund |

(Continued)

FOREIGN PATENT DOCUMENTS

| | | |
|---|---|---|
| DE | 3924291 A1 | 1/1991 |
| DE | 4041614 C1 | 10/1992 |

(Continued)

*Primary Examiner* — Sean Dougherty

(57) ABSTRACT

A biopsy apparatus includes a biopsy probe having a biopsy cannula and a sample basket arranged coaxially about a longitudinal axis. The sample basket is movably disposed relative to the biopsy cannula along the longitudinal axis from a tissue harvesting position to a tissue sample retrieval region. The sample basket has a sample notch formed as an elongate recessed region for receiving a tissue sample. A tissue sample retrieval mechanism includes a sample collection tank configured for removable insertion into a sample tank receptacle. The sample tank receptacle permits movement of the sample collection tank in a direction perpendicular to the longitudinal axis and prohibits movement of the sample collection tank in a direction along the longitudinal axis. The sample collection tank is configured to retrieve the tissue sample directly from the sample notch as the sample basket is moving along the longitudinal axis at the tissue sample retrieval region.

20 Claims, 13 Drawing Sheets

U.S. PATENT DOCUMENTS

| | | |
|---|---|---|
| 4,616,215 A | 10/1986 | Maddalena |
| 4,617,430 A | 10/1986 | Bryant |
| 4,620,539 A | 11/1986 | Andrews et al. |
| 4,643,197 A | 2/1987 | Greene et al. |
| 4,645,153 A | 2/1987 | Granzow et al. |
| 4,678,459 A | 7/1987 | Onik et al. |
| 4,696,298 A | 9/1987 | Higgins et al. |
| 4,702,260 A | 10/1987 | Wang |
| 4,706,687 A | 11/1987 | Rogers |
| 4,776,346 A | 10/1988 | Beraha et al. |
| 4,844,087 A | 7/1989 | Garg |
| 4,850,354 A | 7/1989 | McGurk-Burleson et al. |
| 4,893,635 A | 1/1990 | de Groot et al. |
| 4,907,598 A | 3/1990 | Bauer |
| RE33,258 E | 7/1990 | Onik et al. |
| 4,940,061 A | 7/1990 | Terwilliger et al. |
| 4,952,817 A | 8/1990 | Bolan et al. |
| 4,958,625 A | 9/1990 | Bates et al. |
| 4,967,762 A | 11/1990 | DeVries |
| 4,986,278 A | 1/1991 | Ravid et al. |
| 4,986,279 A | 1/1991 | O'Neill |
| 4,986,807 A | 1/1991 | Farr |
| 4,989,614 A | 2/1991 | Dejter, Jr. et al. |
| 5,025,797 A | 6/1991 | Baran |
| 5,057,822 A | 10/1991 | Hoffman |
| 5,125,413 A | 6/1992 | Baran |
| 5,138,245 A | 8/1992 | Mattinger et al. |
| 5,146,921 A | 9/1992 | Terwilliger et al. |
| 5,158,528 A | 10/1992 | Walker et al. |
| 5,176,628 A | 1/1993 | Charles et al. |
| 5,225,763 A | 7/1993 | Krohn et al. |
| 5,234,000 A | 8/1993 | Hakky et al. |
| 5,236,334 A | 8/1993 | Bennett |
| 5,242,404 A | 9/1993 | Conley et al. |
| 5,249,583 A | 10/1993 | Mallaby |
| 5,282,476 A | 2/1994 | Terwilliger |
| 5,282,477 A | 2/1994 | Bauer |
| 5,324,306 A | 6/1994 | Makower et al. |
| 5,334,183 A | 8/1994 | Wuchinich |
| 5,368,029 A | 11/1994 | Holcombe et al. |
| 5,368,045 A | 11/1994 | Clement et al. |
| 5,400,798 A | 3/1995 | Baran |
| 5,439,474 A | 8/1995 | Li |
| 5,458,112 A | 10/1995 | Weaver |
| 5,469,860 A | 11/1995 | De Santis |
| 5,479,486 A | 12/1995 | Saji |
| 5,485,917 A | 1/1996 | Early |
| 5,492,130 A | 2/1996 | Chiou |
| 5,496,860 A | 3/1996 | Matsumoto et al. |
| 5,511,556 A | 4/1996 | DeSantis |
| 5,526,822 A | 6/1996 | Burbank et al. |
| 5,535,755 A | 7/1996 | Heske |
| 5,546,957 A | 8/1996 | Heske |
| 5,554,151 A | 9/1996 | Hinchliffe |
| 5,560,373 A | 10/1996 | De Santis |
| 5,564,436 A | 10/1996 | Hakky et al. |
| 5,569,284 A | 10/1996 | Young et al. |
| 5,575,293 A | 11/1996 | Miller et al. |
| 5,591,170 A | 1/1997 | Spievack et al. |
| 5,601,585 A | 2/1997 | Banik et al. |
| 5,602,449 A | 2/1997 | Krause et al. |
| 5,617,874 A | 4/1997 | Baran |
| 5,649,547 A | 7/1997 | Ritchart et al. |
| 5,655,542 A | 8/1997 | Weilandt |
| 5,655,657 A | 8/1997 | Roshdy |
| 5,665,101 A | 9/1997 | Becker et al. |
| 5,669,394 A | 9/1997 | Bergey et al. |
| 5,699,909 A | 12/1997 | Foster |
| 5,700,265 A | 12/1997 | Romano |
| 5,709,697 A | 1/1998 | Ratcliff et al. |
| 5,720,760 A | 2/1998 | Becker et al. |
| 5,735,264 A | 4/1998 | Siczek et al. |
| 5,752,923 A | 5/1998 | Terwilliger |
| 5,755,714 A | 5/1998 | Murphy-Chutorian |
| 5,766,135 A | 6/1998 | Terwilliger |
| 5,769,086 A | 6/1998 | Ritchart et al. |
| 5,769,795 A | 6/1998 | Terwilliger |
| 5,775,333 A | 7/1998 | Burbank et al. |
| 5,788,651 A | 8/1998 | Weilandt |
| 5,792,167 A | 8/1998 | Kablik et al. |
| 5,807,282 A | 9/1998 | Fowler |
| 5,817,033 A | 10/1998 | DeSantis et al. |
| 5,817,034 A | 10/1998 | Milliman et al. |
| 5,823,970 A | 10/1998 | Terwilliger |
| 5,827,305 A | 10/1998 | Gordon |
| 5,830,219 A | 11/1998 | Bird et al. |
| D403,405 S | 12/1998 | Terwilliger |
| 5,857,982 A | 1/1999 | Milliman et al. |
| 5,879,365 A | 3/1999 | Whitfield et al. |
| 5,908,233 A | 6/1999 | Heskett et al. |
| 5,913,857 A | 6/1999 | Ritchart et al. |
| 5,916,198 A | 6/1999 | Dillow |
| 5,916,229 A | 6/1999 | Evans |
| 5,928,164 A | 7/1999 | Burbank et al. |
| 5,944,673 A | 8/1999 | Gregoire et al. |
| 5,951,490 A | 9/1999 | Fowler |
| 5,951,575 A | 9/1999 | Bolduc et al. |
| 5,964,716 A | 10/1999 | Gregoire et al. |
| 5,971,939 A | 10/1999 | DeSantis et al. |
| 5,976,164 A | 11/1999 | Bencini et al. |
| 5,980,469 A | 11/1999 | Burbank et al. |
| 5,980,545 A | 11/1999 | Pacala et al. |
| 6,007,495 A | 12/1999 | Matula |
| 6,007,497 A | 12/1999 | Huitema |
| 6,007,556 A | 12/1999 | Kablik et al. |
| 6,017,316 A | 1/2000 | Ritchart et al. |
| 6,018,227 A | 1/2000 | Kumar et al. |
| 6,019,733 A | 2/2000 | Farascioni |
| 6,022,324 A | 2/2000 | Skinner |
| 6,022,325 A | 2/2000 | Siczek et al. |
| 6,027,458 A | 2/2000 | Janssens |
| 6,036,657 A | 3/2000 | Milliman et al. |
| 6,050,955 A | 4/2000 | Bryan et al. |
| 6,055,870 A | 5/2000 | Jaeger |
| 6,077,230 A | 6/2000 | Gregoire et al. |
| 6,083,176 A | 7/2000 | Terwilliger |
| 6,083,237 A | 7/2000 | Huitema et al. |
| 6,086,544 A | 7/2000 | Hibner et al. |
| 6,106,484 A | 8/2000 | Terwilliger |
| 6,110,129 A | 8/2000 | Terwilliger |
| 6,120,462 A | 9/2000 | Hibner et al. |
| 6,123,957 A | 9/2000 | Jernberg |
| 6,126,617 A | 10/2000 | Weilandt et al. |
| 6,142,955 A | 11/2000 | Farascioni et al. |
| 6,162,187 A | 12/2000 | Buzzard et al. |
| 6,165,136 A | 12/2000 | Nishtala |
| 6,193,673 B1 | 2/2001 | Viola et al. |
| 6,196,978 B1 | 3/2001 | Weilandt et al. |
| 6,213,957 B1 | 4/2001 | Milliman et al. |
| 6,220,248 B1 | 4/2001 | Voegele et al. |
| 6,231,522 B1 | 5/2001 | Voegele et al. |
| 6,241,687 B1 | 6/2001 | Voegele et al. |
| 6,267,759 B1 | 7/2001 | Quick |
| 6,273,861 B1 | 8/2001 | Bates et al. |
| 6,273,862 B1 | 8/2001 | Privitera et al. |
| 6,280,398 B1 | 8/2001 | Ritchart et al. |
| 6,283,925 B1 | 9/2001 | Terwilliger |
| 6,322,523 B2 | 11/2001 | Weilandt et al. |
| 6,328,701 B1 | 12/2001 | Terwilliger |
| 6,331,166 B1 | 12/2001 | Burbank et al. |
| 6,358,217 B1 | 3/2002 | Bourassa |
| 6,402,701 B1 | 6/2002 | Kaplan et al. |
| 6,419,641 B1 | 7/2002 | Mark et al. |
| 6,428,486 B2 | 8/2002 | Ritchart et al. |
| 6,428,487 B1 | 8/2002 | Burdorff et al. |
| 6,432,064 B1 | 8/2002 | Hibner et al. |
| 6,432,065 B1 | 8/2002 | Burdorff et al. |
| 6,434,507 B1 | 8/2002 | Clayton et al. |
| 6,436,054 B1 | 8/2002 | Viola et al. |
| 6,471,659 B2 | 10/2002 | Eggers et al. |
| 6,482,158 B2 | 11/2002 | Mault |
| 6,485,436 B1 | 11/2002 | Truckai et al. |
| 6,488,636 B2 | 12/2002 | Bryan et al. |
| 6,527,736 B1 | 3/2003 | Attinger et al. |
| 6,540,694 B1 | 4/2003 | Van Bladel et al. |
| 6,540,761 B2 | 4/2003 | Houser |
| 6,551,255 B2 | 4/2003 | Van Bladel et al. |

| | | | | | |
|---|---|---|---|---|---|
| 6,554,779 B2 | 4/2003 | Viola et al. | 2003/0130677 A1 | 7/2003 | Whitman et al. |
| 6,585,664 B2 | 7/2003 | Burdorff et al. | 2003/0163142 A1 | 8/2003 | Paltieli et al. |
| 6,585,694 B1 | 7/2003 | Smith et al. | 2003/0229293 A1 | 12/2003 | Hibner et al. |
| 6,638,235 B2 | 10/2003 | Miller et al. | 2003/0233101 A1 | 12/2003 | Lubock et al. |
| 6,656,133 B2 | 12/2003 | Voegele et al. | 2004/0015079 A1 | 1/2004 | Berger et al. |
| 6,659,105 B2 | 12/2003 | Burbank et al. | 2004/0019297 A1 | 1/2004 | Angel |
| 6,659,338 B1 | 12/2003 | Dittmann et al. | 2004/0030367 A1 | 2/2004 | Yamaki et al. |
| 6,683,439 B2 | 1/2004 | Takano et al. | 2004/0049128 A1 | 3/2004 | Miller et al. |
| 6,689,072 B2 | 2/2004 | Kaplan et al. | 2004/0054299 A1 | 3/2004 | Burdorff et al. |
| 6,695,786 B2 | 2/2004 | Wang et al. | 2004/0092992 A1 | 5/2004 | Adams et al. |
| 6,712,773 B1 | 3/2004 | Viola | 2004/0167427 A1 | 8/2004 | Quick et al. |
| 6,712,774 B2 | 3/2004 | Voegele et al. | 2004/0186393 A1 | 9/2004 | Leigh et al. |
| 6,752,768 B2 | 6/2004 | Burdorff et al. | 2004/0210161 A1 | 10/2004 | Burdorff et al. |
| 6,753,671 B1 | 6/2004 | Harvey | 2004/0215103 A1 | 10/2004 | Mueller, Jr. et al. |
| 6,758,824 B1 | 7/2004 | Miller et al. | 2004/0220495 A1 | 11/2004 | Cahir et al. |
| 6,764,495 B2 | 7/2004 | Lee et al. | 2004/0249278 A1 | 12/2004 | Krause |
| 6,832,990 B2 | 12/2004 | Kortenbach et al. | 2004/0267157 A1 | 12/2004 | Miller et al. |
| 6,849,080 B2 | 2/2005 | Lee et al. | 2005/0004492 A1 | 1/2005 | Burbank et al. |
| 6,908,440 B2 | 6/2005 | Fisher | 2005/0004559 A1 | 1/2005 | Quick et al. |
| D508,458 S | 8/2005 | Solland et al. | 2005/0010131 A1 | 1/2005 | Burbank et al. |
| 6,926,676 B2 | 8/2005 | Turturro et al. | 2005/0020909 A1 | 1/2005 | Moctezuma de la Barrera et al. |
| 6,984,213 B2 | 1/2006 | Horner et al. | 2005/0027210 A1 | 2/2005 | Miller |
| 7,010,332 B1 | 3/2006 | Irvin et al. | 2005/0049489 A1 | 3/2005 | Foerster et al. |
| 7,025,732 B2 | 4/2006 | Thompson et al. | 2005/0049521 A1 | 3/2005 | Miller et al. |
| D525,583 S | 7/2006 | Vu | 2005/0080355 A1 | 4/2005 | Mark |
| 7,153,274 B2 | 12/2006 | Stephens et al. | 2005/0085838 A1 | 4/2005 | Thompson et al. |
| 7,189,206 B2 | 3/2007 | Quick et al. | 2005/0088120 A1 | 4/2005 | Avis |
| 7,189,207 B2 | 3/2007 | Viola | 2005/0101879 A1 | 5/2005 | Shidham et al. |
| 7,219,867 B2 | 5/2007 | Kalis et al. | 2005/0113715 A1 | 5/2005 | Schwindt et al. |
| 7,226,424 B2 | 6/2007 | Ritchart et al. | 2005/0113716 A1 | 5/2005 | Mueller, Jr. et al. |
| 7,252,641 B2 | 8/2007 | Thompson et al. | 2005/0124914 A1 | 6/2005 | Dicarlo et al. |
| 7,276,032 B2 | 10/2007 | Hibner | 2005/0124915 A1 | 6/2005 | Eggers et al. |
| 7,328,794 B2 | 2/2008 | Lubs et al. | 2005/0165328 A1 | 7/2005 | Heske et al. |
| 7,347,828 B2 | 3/2008 | Francese et al. | 2005/0177117 A1 | 8/2005 | Crocker et al. |
| 7,347,829 B2 | 3/2008 | Mark et al. | 2005/0193451 A1 | 9/2005 | Quistgaard et al. |
| 7,374,544 B2 | 5/2008 | Freeman et al. | 2005/0203439 A1 | 9/2005 | Heske et al. |
| 7,397,654 B2 | 7/2008 | Mori | 2005/0209530 A1 | 9/2005 | Pflueger |
| 7,402,140 B2 | 7/2008 | Spero et al. | 2005/0275378 A1 | 12/2005 | Canino et al. |
| 7,405,536 B2 | 7/2008 | Watts | 2005/0277829 A1 | 12/2005 | Tsonton et al. |
| 7,407,054 B2 | 8/2008 | Seiler et al. | 2005/0277871 A1 | 12/2005 | Selis |
| 7,432,813 B2 | 10/2008 | Postma | 2005/0288605 A1 | 12/2005 | Pellegrino et al. |
| 7,452,367 B2 | 11/2008 | Rassman et al. | 2006/0030784 A1 | 2/2006 | Miller et al. |
| 7,464,040 B2 | 12/2008 | Joao | 2006/0074344 A1 | 4/2006 | Hibner |
| 7,473,232 B2 | 1/2009 | Teague | 2006/0074345 A1 | 4/2006 | Hibner |
| 7,481,775 B2 | 1/2009 | Weikel, Jr. et al. | 2006/0113958 A1 | 6/2006 | Lobert et al. |
| 7,490,048 B2 | 2/2009 | Joao | 2006/0116603 A1 | 6/2006 | Shibazaki et al. |
| 7,513,877 B2 | 4/2009 | Viola | 2006/0129063 A1 | 6/2006 | Thompson et al. |
| 7,517,321 B2 | 4/2009 | McCullough et al. | 2006/0173377 A1 | 8/2006 | McCullough et al. |
| 7,517,322 B2 | 4/2009 | Weikel, Jr. et al. | 2006/0178666 A1 | 8/2006 | Cosman et al. |
| 7,648,466 B2 | 1/2010 | Stephens et al. | 2006/0184063 A1 | 8/2006 | Miller |
| 7,670,299 B2 | 3/2010 | Beckman et al. | 2006/0241515 A1 | 10/2006 | Jones et al. |
| 7,717,861 B2 | 5/2010 | Weikel et al. | 2006/0258956 A1 | 11/2006 | Haberstich et al. |
| 7,727,164 B2 | 6/2010 | Cicenas et al. | 2007/0016101 A1 | 1/2007 | Feldman et al. |
| 7,740,594 B2 | 6/2010 | Hibner | 2007/0027407 A1 | 2/2007 | Miller |
| 7,740,596 B2 | 6/2010 | Hibner | 2007/0032741 A1 | 2/2007 | Hibner et al. |
| 7,740,597 B2 | 6/2010 | Cicenas et al. | 2007/0073326 A1 | 3/2007 | Miller et al. |
| 7,762,961 B2 | 7/2010 | Heske et al. | 2007/0090788 A1 | 4/2007 | Hansford et al. |
| 7,828,746 B2 | 11/2010 | Teague | 2007/0106176 A1 | 5/2007 | Mark et al. |
| 7,854,706 B2 | 12/2010 | Hibner | 2007/0118048 A1 | 5/2007 | Stephens et al. |
| 7,883,476 B2 | 2/2011 | Miller et al. | 2007/0118049 A1 | 5/2007 | Viola |
| 7,974,681 B2 | 7/2011 | Wallace et al. | 2007/0149894 A1 | 6/2007 | Heske et al. |
| 8,073,008 B2 | 12/2011 | Mehta et al. | 2007/0161925 A1 | 7/2007 | Quick et al. |
| 8,190,238 B2 | 5/2012 | Moll et al. | 2007/0167782 A1 | 7/2007 | Callahan et al. |
| 2001/0007925 A1 | 7/2001 | Ritchart et al. | 2007/0167828 A1 | 7/2007 | Saadat |
| 2001/0011156 A1 | 8/2001 | Viola et al. | 2007/0167943 A1 | 7/2007 | Janssen et al. |
| 2001/0012919 A1 | 8/2001 | Terwilliger | 2007/0179401 A1* | 8/2007 | Hibner .................. 600/567 |
| 2001/0014779 A1 | 8/2001 | Burbank et al. | 2007/0213590 A1 | 9/2007 | Squicciarini |
| 2001/0034530 A1 | 10/2001 | Malackowski et al. | 2007/0213630 A1 | 9/2007 | Beckman et al. |
| 2001/0044595 A1 | 11/2001 | Reydel et al. | 2007/0213632 A1 | 9/2007 | Okazaki et al. |
| 2001/0047183 A1 | 11/2001 | Privitera et al. | 2007/0219572 A1 | 9/2007 | Deck et al. |
| 2002/0029007 A1 | 3/2002 | Bryan et al. | 2007/0236180 A1 | 10/2007 | Rodgers |
| 2002/0065474 A1 | 5/2002 | Viola | 2007/0239067 A1 | 10/2007 | Hibner et al. |
| 2002/0067151 A1 | 6/2002 | Tanishita | 2007/0255173 A1 | 11/2007 | Hibner |
| 2002/0068878 A1 | 6/2002 | Jasonni et al. | 2007/0270710 A1 | 11/2007 | Frass et al. |
| 2002/0082518 A1 | 6/2002 | Weiss et al. | 2007/0276288 A1 | 11/2007 | Khaw |
| 2002/0107043 A1 | 8/2002 | Adamson et al. | 2007/0287933 A1 | 12/2007 | Phan et al. |
| 2002/0120212 A1 | 8/2002 | Ritchart et al. | 2007/0293788 A1 | 12/2007 | Entrekin et al. |
| 2002/0156395 A1 | 10/2002 | Stephens et al. | 2008/0004545 A1 | 1/2008 | Garrison |
| 2003/0130593 A1 | 7/2003 | Gonzalez | 2008/0007217 A1 | 1/2008 | Riley |

| | | | |
|---|---|---|---|
| 2008/0015429 A1 | 1/2008 | Tsonton et al. | |
| 2008/0021487 A1 | 1/2008 | Heisler | |
| 2008/0021488 A1 | 1/2008 | Berberich | |
| 2008/0030170 A1 | 2/2008 | Dacquay et al. | |
| 2008/0064925 A1 | 3/2008 | Gill et al. | |
| 2008/0064984 A1 | 3/2008 | Pflueger | |
| 2008/0071193 A1 | 3/2008 | Reuber et al. | |
| 2008/0079391 A1 | 4/2008 | Schroeck et al. | |
| 2008/0110261 A1 | 5/2008 | Randall et al. | |
| 2008/0135443 A1 | 6/2008 | Frojd et al. | |
| 2008/0146962 A1 | 6/2008 | Ritchie et al. | |
| 2008/0146965 A1 | 6/2008 | Privitera et al. | |
| 2008/0154151 A1 | 6/2008 | Ritchart et al. | |
| 2008/0161682 A1 | 7/2008 | Kendrick et al. | |
| 2008/0161718 A1 | 7/2008 | Schwindt | |
| 2008/0161719 A1 | 7/2008 | Miller et al. | |
| 2008/0161720 A1 | 7/2008 | Nicoson et al. | |
| 2008/0183099 A1 | 7/2008 | Jorgensen et al. | |
| 2008/0195066 A1 | 8/2008 | Speeg et al. | |
| 2008/0200833 A1 | 8/2008 | Hardin et al. | |
| 2008/0200836 A1 | 8/2008 | Speeg et al. | |
| 2008/0208194 A1 | 8/2008 | Bickenbach | |
| 2008/0214955 A1 | 9/2008 | Speeg et al. | |
| 2008/0215056 A1 | 9/2008 | Miller et al. | |
| 2008/0221443 A1 | 9/2008 | Ritchie et al. | |
| 2008/0221444 A1 | 9/2008 | Ritchie et al. | |
| 2008/0221478 A1 | 9/2008 | Ritchie et al. | |
| 2008/0221479 A1 | 9/2008 | Ritchie et al. | |
| 2008/0221480 A1 | 9/2008 | Hibner et al. | |
| 2008/0228104 A1 | 9/2008 | Uber et al. | |
| 2008/0232604 A1 | 9/2008 | Dufresne et al. | |
| 2008/0234715 A1 | 9/2008 | Pesce et al. | |
| 2008/0281225 A1 | 11/2008 | Spero et al. | |
| 2008/0287826 A1 | 11/2008 | Videbaek et al. | |
| 2008/0306406 A1 | 12/2008 | Thompson et al. | |
| 2008/0308607 A1 | 12/2008 | Timm et al. | |
| 2008/0319341 A1 | 12/2008 | Taylor et al. | |
| 2009/0030405 A1 | 1/2009 | Quick et al. | |
| 2009/0062624 A1 | 3/2009 | Neville | |
| 2009/0082695 A1 | 3/2009 | Whitehead | |
| 2009/0125062 A1 | 5/2009 | Arnin | |
| 2009/0137927 A1 | 5/2009 | Miller | |
| 2009/0171243 A1 | 7/2009 | Hibner et al. | |
| 2009/0227893 A1 | 9/2009 | Coonahan et al. | |
| 2010/0030020 A1 | 2/2010 | Sanders et al. | |
| 2010/0030108 A1 | 2/2010 | Anderson et al. | |
| 2010/0063416 A1 | 3/2010 | Cicenas et al. | |
| 2010/0106053 A1 | 4/2010 | Videbaek et al. | |
| 2010/0152611 A1 | 6/2010 | Parihar et al. | |
| 2010/0160820 A1 | 6/2010 | Weikel, Jr. et al. | |
| 2010/0210966 A1 | 8/2010 | Videbaek | |
| 2010/0292607 A1 | 11/2010 | Moore et al. | |
| 2010/0312140 A1 | 12/2010 | Smith et al. | |
| 2010/0317995 A1 | 12/2010 | Hibner et al. | |
| 2010/0317997 A1 | 12/2010 | Hibner et al. | |
| 2010/0317998 A1 | 12/2010 | Hibner et al. | |
| 2011/0077551 A1 | 3/2011 | Videbaek | |
| 2011/0087131 A1 | 4/2011 | Videbaek | |
| 2011/0105945 A1 | 5/2011 | Videbaek et al. | |
| 2011/0105946 A1 | 5/2011 | Sorensen et al. | |
| 2011/0152715 A1 | 6/2011 | Delap et al. | |
| 2011/0160611 A1 | 6/2011 | Ritchart et al. | |

FOREIGN PATENT DOCUMENTS

| | | | |
|---|---|---|---|
| DE | 10034297 | A1 | 4/2001 |
| DE | 10026303 | A1 | 2/2002 |
| DE | 20209525 | U1 | 11/2002 |
| DE | 10235480 | A1 | 2/2004 |
| EP | 0433717 | A1 | 6/1991 |
| EP | 0890339 | A1 | 1/1999 |
| EP | 0995400 | A1 | 4/2000 |
| EP | 1074271 | A2 | 2/2001 |
| EP | 1520518 | A2 | 4/2005 |
| EP | 1579809 | A1 | 9/2005 |
| EP | 1665989 | A2 | 6/2006 |
| EP | 2095772 | A1 | 9/2009 |
| EP | 2106750 | A2 | 10/2009 |
| FR | 1345429 | A | 12/1963 |
| FR | 2739293 | A1 | 4/1997 |
| GB | 2018601 | A | 10/1979 |
| JP | H10508504 | A | 8/1998 |
| JP | 2005530554 | A | 10/2005 |
| JP | 2006509545 | A | 3/2006 |
| JP | 2006528907 | A | 12/2006 |
| JP | 2007502159 | A | 2/2007 |
| WO | 9508945 | A2 | 4/1995 |
| WO | 9624289 | A2 | 8/1996 |
| WO | 9628097 | A1 | 9/1996 |
| WO | 9825522 | A1 | 6/1998 |
| WO | 9831285 | A1 | 7/1998 |
| WO | 9835615 | A1 | 8/1998 |
| WO | 9846290 | A1 | 10/1998 |
| WO | 9933501 | A1 | 7/1999 |
| WO | 0004832 | A1 | 2/2000 |
| WO | 0030546 | A1 | 6/2000 |
| WO | 0059378 | A2 | 10/2000 |
| WO | 0172230 | A1 | 10/2001 |
| WO | 0222023 | A1 | 3/2002 |
| WO | 0232318 | A1 | 4/2002 |
| WO | 02069808 | A2 | 9/2002 |
| WO | 2005013830 | A1 | 2/2005 |
| WO | 2006015302 | A1 | 2/2006 |
| WO | 2007047128 | A1 | 4/2007 |
| WO | 2007095330 | A2 | 8/2007 |
| WO | 2007112751 | A2 | 10/2007 |
| WO | 2008021687 | A1 | 2/2008 |
| WO | 2008024684 | A2 | 2/2008 |
| WO | 2008040812 | A1 | 4/2008 |
| WO | 2008131362 | A2 | 10/2008 |
| WO | 2010107424 | A1 | 9/2010 |
| WO | 2010120294 | A1 | 10/2010 |
| WO | 2011019343 | A1 | 2/2011 |

* cited by examiner

BIOPSY APPARATUS HAVING A TISSUE SAMPLE RETRIEVAL MECHANISM

CROSS-REFERENCE TO RELATED APPLICATIONS

This application is related to International Application No. PCT/US2009/040663, filed Apr. 15, 2009.

MICROFICHE APPENDIX

None.

GOVERNMENT RIGHTS IN PATENT

None.

BACKGROUND OF THE INVENTION

1. Field of the Invention

The present invention relates to a biopsy apparatus, and, more particularly, to a biopsy apparatus having a tissue sample retrieval mechanism, and a method for retrieving a tissue sample using the same.

2. Description of the Related Art

A biopsy may be performed on a patient to help in determining whether the cells in a biopsied region are cancerous. One type of vacuum assisted biopsy apparatus includes a hand-held driver assembly having a vacuum source, and a disposable biopsy probe assembly configured for releasable attachment to the driver assembly. One biopsy technique used to evaluate breast tissue, for example, involves inserting a biopsy probe into the breast tissue region of interest to capture one or more tissue samples from the region.

The biopsy probe typically includes a biopsy cannula, e.g., a needle, having a cylindrical side wall defining a lumen, and having a side sample notch located near the distal end that extends though the side wall to the lumen. A cutting cannula is positioned coaxial with the biopsy cannula to selectively open and close the sample notch. Vacuum is applied to the lumen, and in turn to the sample notch, for receiving the tissue to be sampled when the sample notch is opened, after which the sample notch is closed by the cutting cannula to sever the tissue, and the severed tissue is transported by vacuum out of the lumen and collected.

SUMMARY OF THE INVENTION

The present invention provides a fully integrated hand-held biopsy apparatus having a tissue sample retrieval mechanism that does not rely on vacuum to transport a harvested tissue sample from the biopsy cannula to a tissue sample collection tank.

As used herein, the terms "first" and "second" preceding an element name, e.g., first drive, second drive, etc., are for identification purposes to distinguish between different elements having similar characteristic, and are not intended to necessarily imply order, unless otherwise specified, nor are the terms "first" and "second" intended to preclude the inclusion of additional similar elements.

The invention, in one form thereof, is directed to a biopsy apparatus. The biopsy apparatus includes an electromechanical power source, a biopsy probe, and a tissue sample retrieval mechanism. The biopsy probe is drivably coupled to the electromechanical power source. The biopsy probe includes a biopsy cannula and a sample basket arranged coaxially about a longitudinal axis. The sample basket is movably disposed relative to the biopsy cannula along the longitudinal axis from a tissue harvesting position to a tissue sample retrieval region. The sample basket has a sample notch formed as an elongate recessed region for receiving a tissue sample. The tissue sample retrieval mechanism includes a sample tank receptacle and a sample collection tank configured for removable insertion into the sample tank receptacle. The sample tank receptacle permits movement of the sample collection tank in a direction perpendicular to the longitudinal axis and prohibits movement of the sample collection tank in a direction along the longitudinal axis. The sample collection tank is configured to retrieve the tissue sample directly from the sample notch as the sample basket is moving along the longitudinal axis at the tissue sample retrieval region.

The invention, in another form thereof, is directed to a biopsy apparatus. The biopsy apparatus includes a driver assembly and a disposable biopsy probe assembly. The driver assembly is configured to be grasped by a user, and has an electromechanical power source. The disposable biopsy probe assembly is configured for releasable attachment to the driver assembly. The disposable biopsy probe assembly includes a transmission device configured for driving engagement with the electromechanical power source. A biopsy probe drivably is coupled to the transmission device. The biopsy probe includes a biopsy cannula and a sample basket arranged coaxially about a longitudinal axis. The sample basket is movably disposed relative to the biopsy cannula along the longitudinal axis from a tissue harvesting position to a tissue sample retrieval region. The sample basket has a sample notch formed as an elongate recessed region for receiving a tissue sample. A tissue sample retrieval mechanism includes a sample tank receptacle and a sample collection tank configured for removable insertion into the sample tank receptacle. The sample tank receptacle permits movement of the sample collection tank in a direction perpendicular to the longitudinal axis and prohibiting movement of the sample collection tank in a direction along the longitudinal axis. The sample collection tank is configured to retrieve the tissue sample directly from the sample notch as the sample basket is moving along the longitudinal axis at the tissue sample retrieval region.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
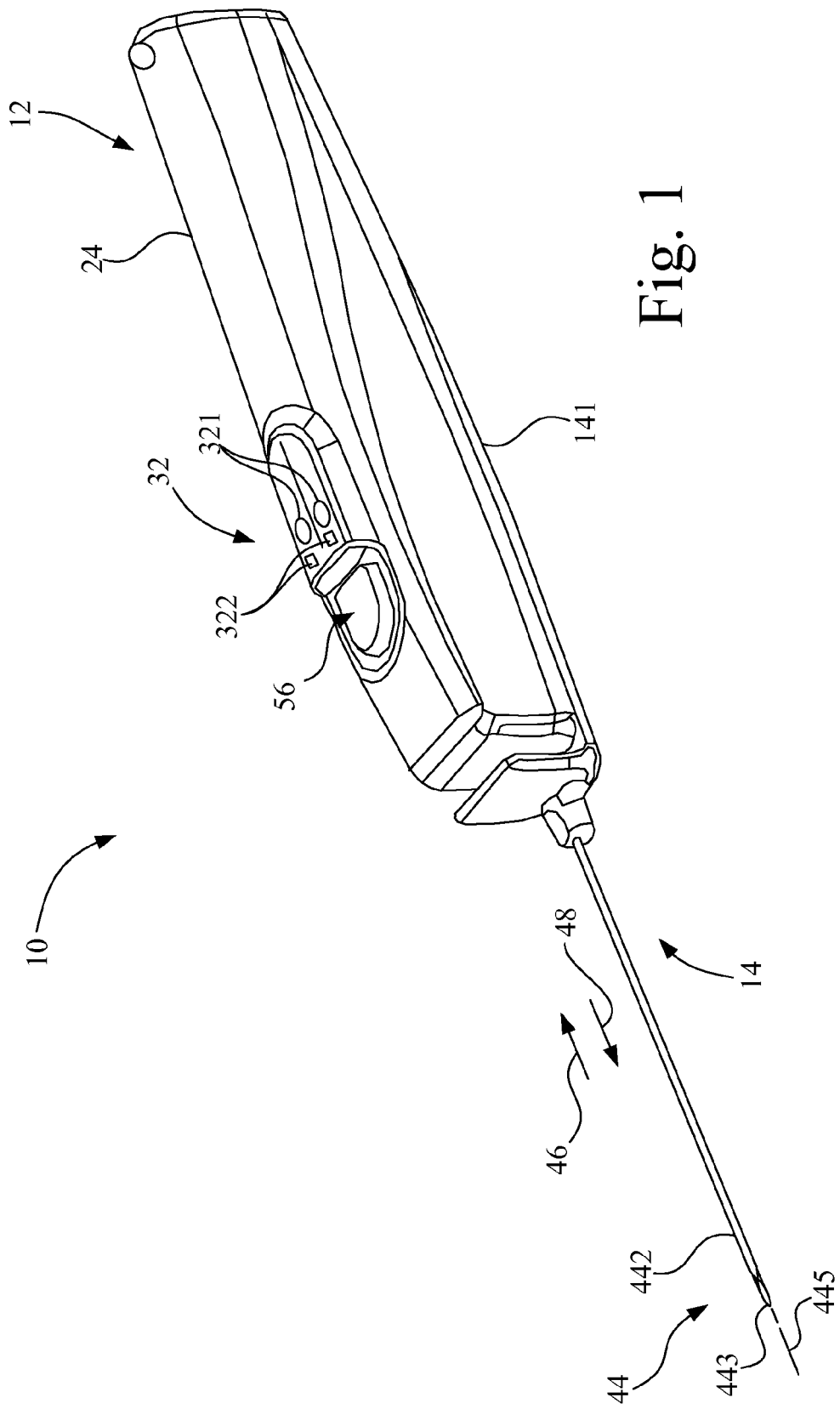
FIG. 1 is a perspective view of a biopsy apparatus, configured in accordance with an embodiment of the present invention, with a disposable biopsy probe mounted to a driver assembly.
Figure 2:
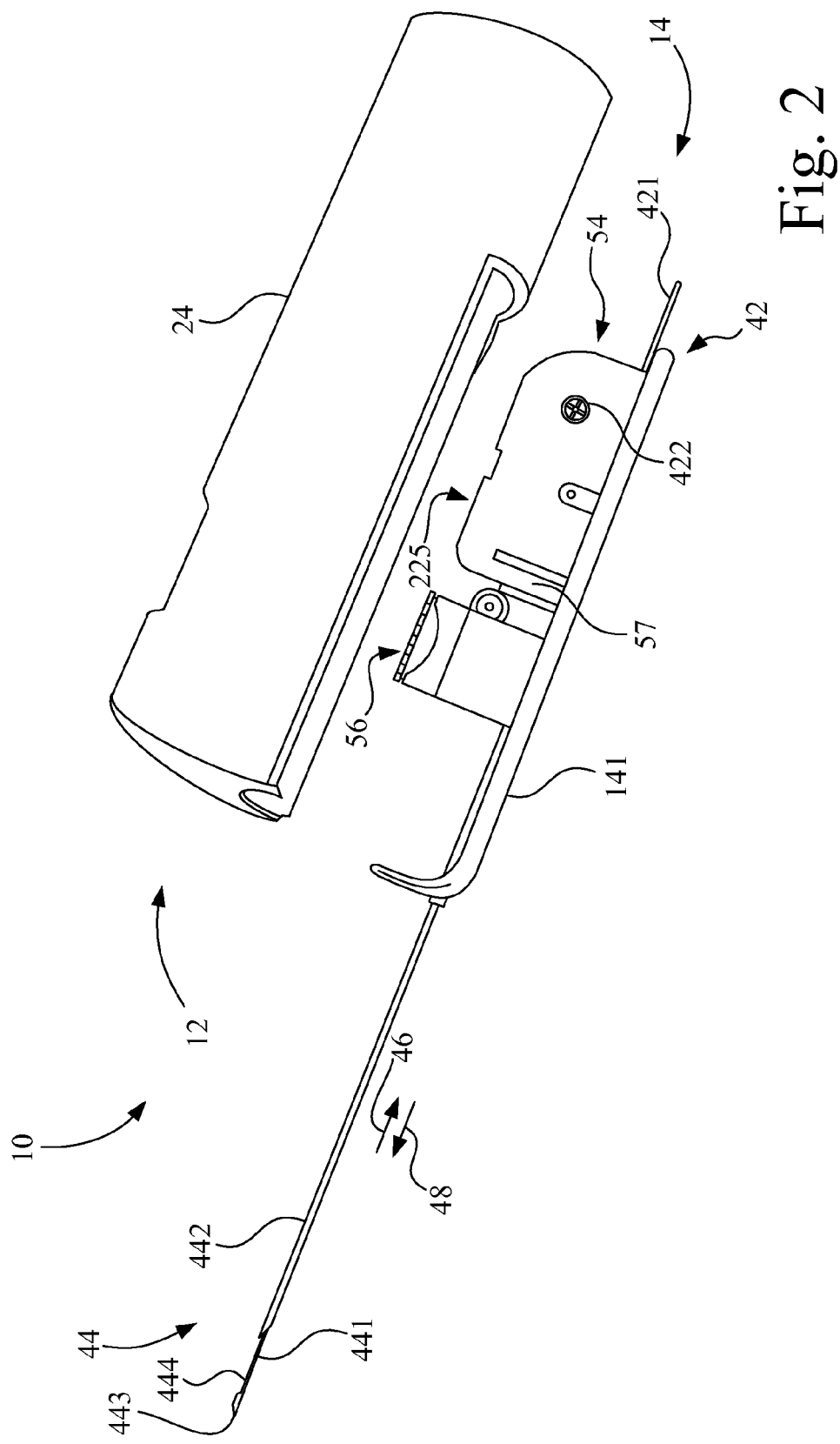
FIG. 2 is a perspective view of a biopsy apparatus of FIG. 1, with the disposable biopsy probe detached from the driver assembly.

Referring now to the drawings, and more particularly to FIGS. 1 and 2, there is shown a biopsy apparatus 10 which generally includes a non-invasive, e.g., non-disposable, driver assembly 12 and a disposable biopsy probe assembly 14.

Figure 3:
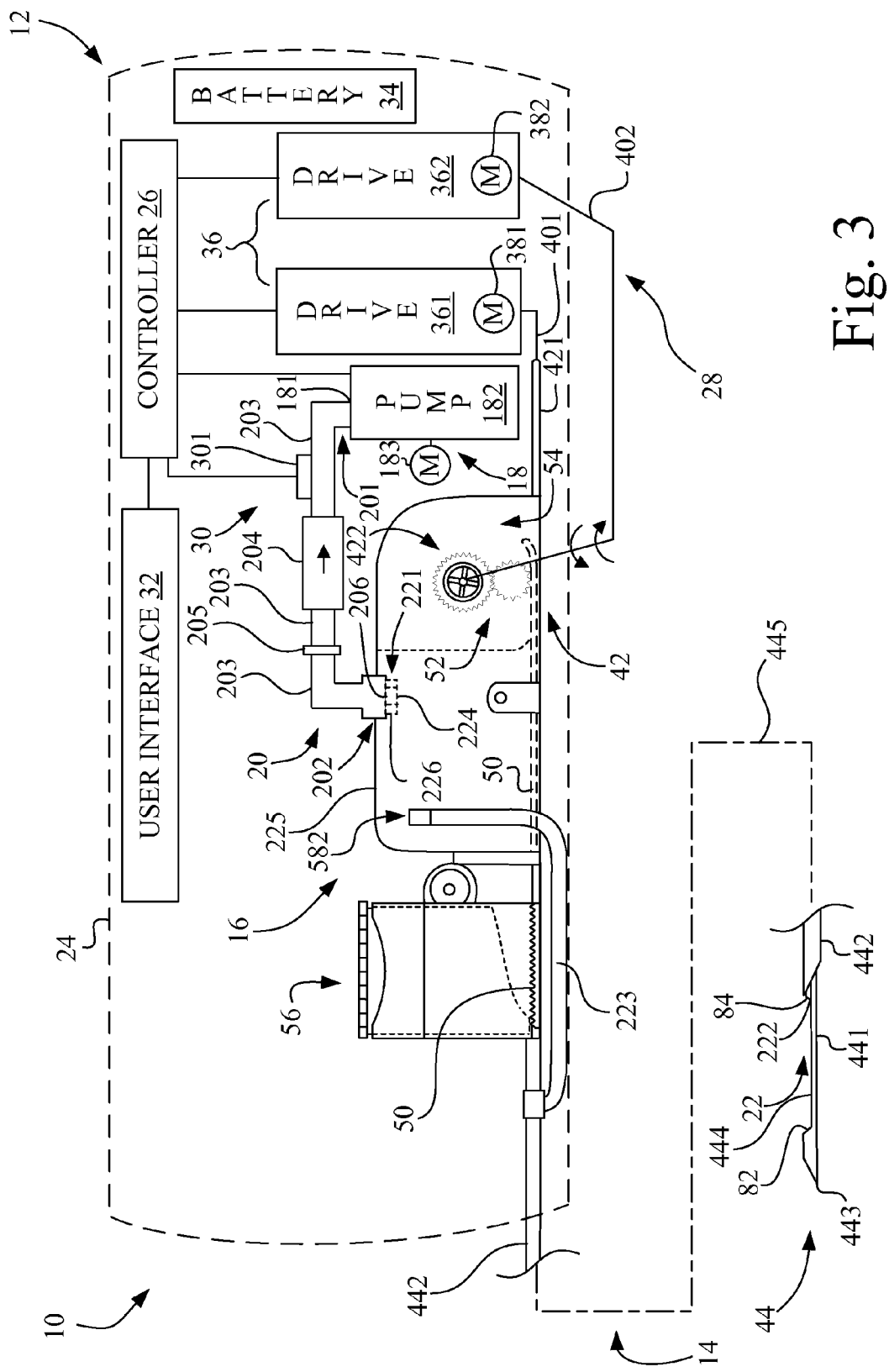
FIG. 3 is a schematic representation of the biopsy apparatus of FIG. 1.

Referring also to FIG. 3, driver assembly 12 and disposable biopsy probe assembly 14 collectively include a fluid management system 16 that includes a vacuum source 18, first vacuum path 20 and a second vacuum path 22. Vacuum source 18 and a first vacuum path 20 are permanently associated with driver assembly 12, and a second vacuum path 22 is permanently associated with disposable biopsy probe assembly 14, as more fully described below, to help facilitate the safe and effective collection of a biopsy tissue sample.

As used herein, the term "non-disposable" is used to refer to a device that is intended for use on multiple patients during the lifetime of the device, and the term "disposable" is used to refer to a device that is intended to be disposed of after use on a single patient. Also, the term "vacuum path" means a fluid passageway used to facilitate a vacuum between two points, the fluid passageway passing through one or more components, such as for example, one or more of tubing, conduits, couplers, and interposed devices. Also, the term "permanently associated" means a connection that is not intended for releasable attachment on a routine basis during the lifetime of the components. Thus, for example, driver assembly 12 including vacuum source 18 and first vacuum path 20 is reusable as a unit in its entirety, whereas disposable biopsy probe assembly 14 and second vacuum path 22 are disposable as a unit in its entirety.

Driver assembly 12 includes a housing 24 configured, and ergonomically designed, to be grasped by a user. Driver assembly 12 includes (contained within housing 24) vacuum source 18, first vacuum path 20, a controller 26, an electromechanical power source 28, and a vacuum monitoring mechanism 30. A user interface 32 is located to be mounted to, and externally accessible with respect to, housing 24.

Controller 26 is communicatively coupled to electromechanical power source 28, vacuum source 18, user interface 32, and vacuum monitoring mechanism 30. Controller 26 may include, for example, a microprocessor and associated memory for executing program instructions to perform functions associated with the retrieval of biopsy tissue samples, such as controlling one or more components of vacuum source 18 and electromechanical power source 28. Controller 26 also may execute program instructions to monitor one or more conditions and/or positions of components of biopsy apparatus 10, and to monitor the status of fluid management system 16 associated with driver assembly 12 and disposable probe assembly 14.

The user interface 32 includes control buttons 321 and visual indicators 322, with control buttons 321 providing user control over various functions of biopsy apparatus 10, and visual indicators 322 providing visual feedback of the status of one or more conditions and/or positions of components of biopsy apparatus 10.

The electromechanical power source 28 may include, for example, an electrical energy source, e.g., battery, 34 and an electrical drive assembly 36. Battery 34 may be, for example, a rechargeable battery. Battery 34 provides electrical power to all electrically powered components in biopsy apparatus 10, and thus for simplicity in the drawings, such electrical couplings are not shown. For example, battery 34 is electrically coupled to vacuum source 18, controller 26, user interface 32 and electrical drive assembly 36.

In the present embodiment, electrical drive assembly 36 includes a first drive 361 and a second drive 362, each being respectively coupled to battery 34, and each of first drive 361 and second drive 362 respectively electrically and controllably coupled to user interface 32.

First drive 361 may include an electrical motor 381 and a motion transfer unit 401 (shown schematically by a line). Second drive 362 may include an electrical motor 382 and a motion transfer unit 402 (shown schematically by a line). Each electrical motor 381, 382 may be, for example, a direct current (DC) motor, stepper motor, etc. Motion transfer unit 401 of first drive 361 may be configured, for example, with a rotational-to-linear motion converter, such as a worm gear arrangement, rack and pinion arrangement, solenoid-slide arrangement, etc. Motion transfer unit 402 of second drive 362 may be configured to transmit rotary motion. Each of first drive 361 and second drive 362 may include one or more of a gear, gear train, belt/pulley arrangement, etc.

Vacuum source 18 is electrically coupled to battery 34, and has a vacuum source port 181 for establishing a vacuum. Vacuum source 18 is electrically and controllably coupled to user interface 32. Vacuum source 18 may further include, for example, a vacuum pump 182 driven by an electric motor

183. Vacuum pump 182 may be, for example, a peristaltic pump, a diaphragm pump, syringe-type pump, etc.

Figure 4A:
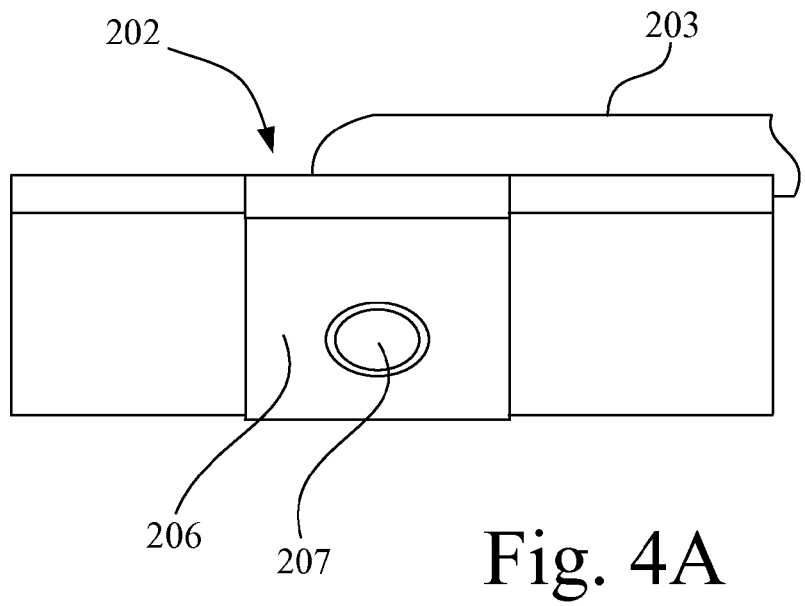
FIG. 4A is a perspective view of a vacuum seal element of the vacuum path of the driver assembly of FIG. 3.

First vacuum path 20 of driver assembly 12 is permanently associated with vacuum source 18. First vacuum path 20, also sometimes referred to as a non-disposable vacuum path, has a proximal end 201 and a distal end 202, and includes, for example, conduits 203, a first one-way valve 204, and a particulate filter 205. Proximal end 201 is fixedly coupled to vacuum source 18 in fluid communication therewith, e.g., is fixedly connected to vacuum source port 181 of vacuum source 18. Referring also to FIG. 4A, distal end 202 includes a first vacuum seal element 206. In the present embodiment, first vacuum seal element 206 is a planar abutment surface that surrounds a first passageway 207 of first vacuum path 20.

First one-way valve 204 is configured and arranged to permit a negative pressure fluid flow toward vacuum source 18 and to prevent a positive pressure fluid flow away from vacuum source 18 toward the distal end 202 of first vacuum path 20. The first one-way valve 204 may be, for example, a check-valve, such as a ball valve or reed valve, that opens with a fluid flow toward vacuum source 18, and closes in the case of a reverse (positive) flow away from vacuum source 18.

In the present embodiment, particulate filter 205 is located between vacuum source 18 and distal end 202 of first vacuum path 20. Particulate filter 205 may be, for example, a mesh screen formed from metal or plastic. However, it is contemplated that particulate filter 205 may be located in fluid management system 16 between vacuum source 18 and a vacuum receiving component of biopsy probe assembly 14.

The vacuum monitoring mechanism 30 is coupled to vacuum source 18 to shut off vacuum source 18 when a sensed vacuum level has fallen below a threshold level. Vacuum monitoring mechanism 30 may include, for example, a vacuum monitor and control program executing on controller 26, and a pressure sensor 301 coupled to controller 26, and in fluid communication with first vacuum path 20 for detecting a pressure in first vacuum path 20. If, for example, the vacuum flow level in first vacuum path 20 falls below a predetermined level, indicating a restriction in fluid management system 16, controller 26 may respond by shutting off vacuum source 18, e.g., turning off electric motor 183. Alternatively, controller 26 may monitor the current supplied to electric motor 183, and if the current exceeds a predetermined amount, indicating a restriction in fluid management system 16, controller 26 may respond by shutting off vacuum source 18, e.g., turning off electric motor 183.

The disposable biopsy probe assembly 14 is configured for releasable attachment to driver assembly 12. As used herein, the term "releasable attachment" means a configuration that facilitates an intended temporary connection followed by selective detachment involving a manipulation of disposable biopsy probe assembly 14 relative to driver assembly 12, without the need for tools.

The disposable biopsy probe assembly 14 includes a frame 141 to which a transmission device 42, a biopsy probe 44, and the second vacuum path 22 are mounted. Biopsy probe 44 is drivably coupled to transmission device 42, and transmission device 42 is drivably coupled to electromechanical power source 28 of driver assembly 12.

In the embodiment shown, transmission device 42 includes a first driven unit 421 and a second driven unit 422 that are drivably engaged with various components of biopsy probe 44. Also, first driven unit 421 is drivably engaged with first drive 361 of electrical drive assembly 36 of driver assembly 12. Second driven unit 422 is drivably engaged with second drive 362 of electrical drive assembly 36 of driver assembly 12.

In the embodiment shown (see, e.g., FIGS. 1-3), biopsy probe 44 includes a sample basket 441 and a cutter cannula 442. Sample basket 441 has a sharpened tip 443 to aid in puncturing tissue and has a sample notch 444 in the form of a recessed region for receiving a biopsy tissue sample. Sample basket 441 and a cutter cannula 442 are configured to be individually movable along a longitudinal axis 445.

In operation, cutter cannula 442 is linearly driven by first driven unit 421 to traverse over sample notch 444 of sample basket 441 along longitudinal axis 445. For example, first driven unit 421 may be in the form of a linear slide that is drivably engaged with first drive 361 of driver assembly 12, which in turn drives cutter cannula 442 along longitudinal axis 445 in a first direction 46, i.e., toward a proximal end of driver assembly 12, to expose sample notch 444 of sample basket 441, and drives cutter cannula 442 in a second direction 48 opposite to first direction 46 to sever tissue prolapsed into sample notch 444. Also, first driven unit 421 and second driven unit 422 may be configured to operate in unison to advance both sample basket 441 and cutter cannula 442 in unison along an longitudinal axis 445 in a piercing shot operation to aid in inserting biopsy probe 44 into fibrous tissue.

The second driven unit 422 may include a flexible toothed rack 50 and a gear train 52. Flexible toothed rack 50 is connected to sample basket 441, and gear train 52 is engaged with the teeth of flexible toothed rack 50. In operation, second drive 362 transfers rotary motion to gear train 52, and in turn gear train 52 engages flexible toothed rack 50 to move sample basket 441 linearly to transport the tissue captured in sample notch 444 out of the body of the patient. Flexible toothed rack 50 is received in a coiling unit 54 when retracting, thereby enabling substantial reduction in the overall device length of biopsy apparatus 10 as compared to a rigid capture system. Each harvested tissue sample is transported out of the body of the patient and is collected by tissue sample retrieval mechanism 56, which scoops the tissue sample out of sample notch 444. In the present embodiment, coiling unit 54 and tissue sample retrieval mechanism 56 are as an integral unit with a housing 57 that is common to coiling unit 54 and tissue sample retrieval mechanism 56. Housing 57 is attached to frame 141. Tissue sample retrieval mechanism 56 will be described in greater detail later.

In the present embodiment, the second vacuum path 22, also sometimes referred to as a disposable vacuum path 22, has a first end 221 and a second end 222, and includes for example, conduits 223, a second one-way valve 224, and a fluid management tank 225. The first end 221 is configured for removable attachment to the distal end 202 of the first vacuum path 20 of driver assembly 12. The second end 222 is coupled in fluid communication with sample basket 441, and more particularly, is coupled in fluid communication with sample notch 444 of sample basket 441.

Figure 4B:
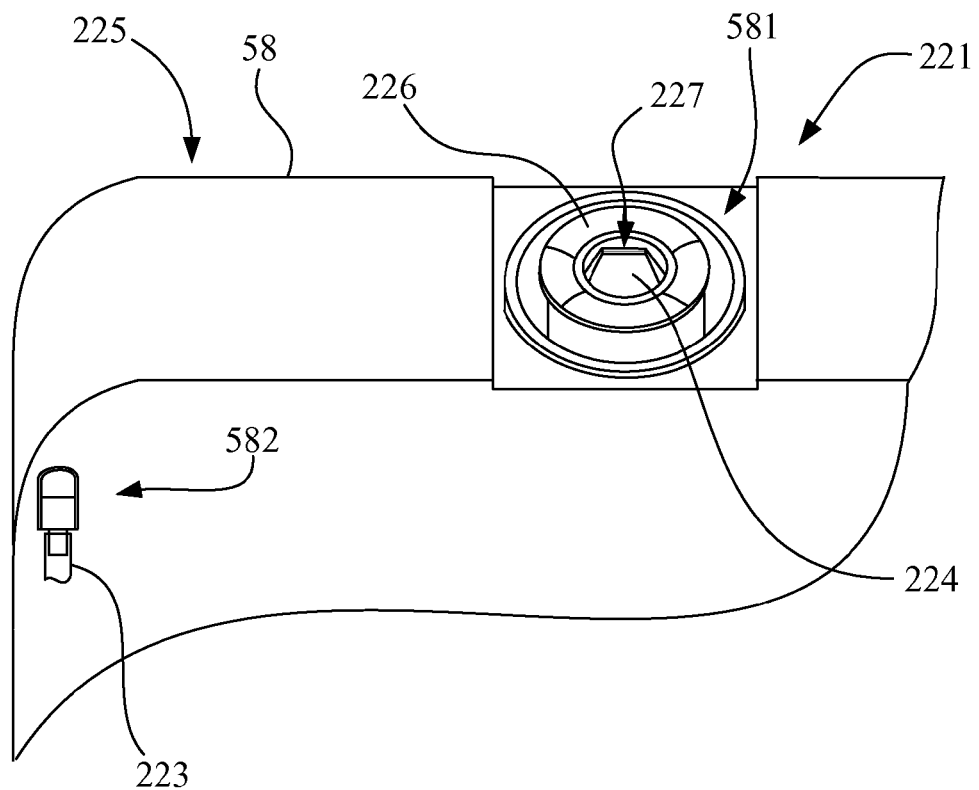
FIG. 4B is a perspective view of a vacuum seal element of the vacuum path of the disposable biopsy probe of FIG. 3.

Referring also to FIG. 4B, the first end 221 of the disposable vacuum path 22 includes a second vacuum seal element 226. The first vacuum seal element 206 of the driver assembly 12 contacts the second vacuum seal element 226 of the disposable biopsy probe assembly 14 in sealing engagement when the disposable biopsy probe assembly 14 is attached to driver assembly 12. The second vacuum seal element 226 is a compliant, e.g., rubber, annular member that surrounds a second passageway 227 of the second vacuum path 22.

The second one-way valve 224 configured and arranged to permit the negative pressure fluid flow from sample basket 441 toward the first end 221 of the second vacuum path 22, and to redundantly (in conjunction with first one-way valve 204 of driver assembly 12) prevent any positive pressure fluid flow in a direction from the first end 221 of the second vacuum path 22 toward sample basket 441. In other words, the second one-way valve 224 provides a redundant second level of protection in preventing any positive pressure from reaching sample notch 444 of sample basket 441. In the present embodiment, the second one-way valve 224 may be, for example, a duckbill valve, e.g., a reed-type valve, that opens with a fluid flow out the bill portion of the duckbill valve, and closes with a reverse flow. As shown, the second one-way valve 224 may be positioned within the second vacuum seal element 226 at first end 221 of second vacuum path 22.

Figure 5A:
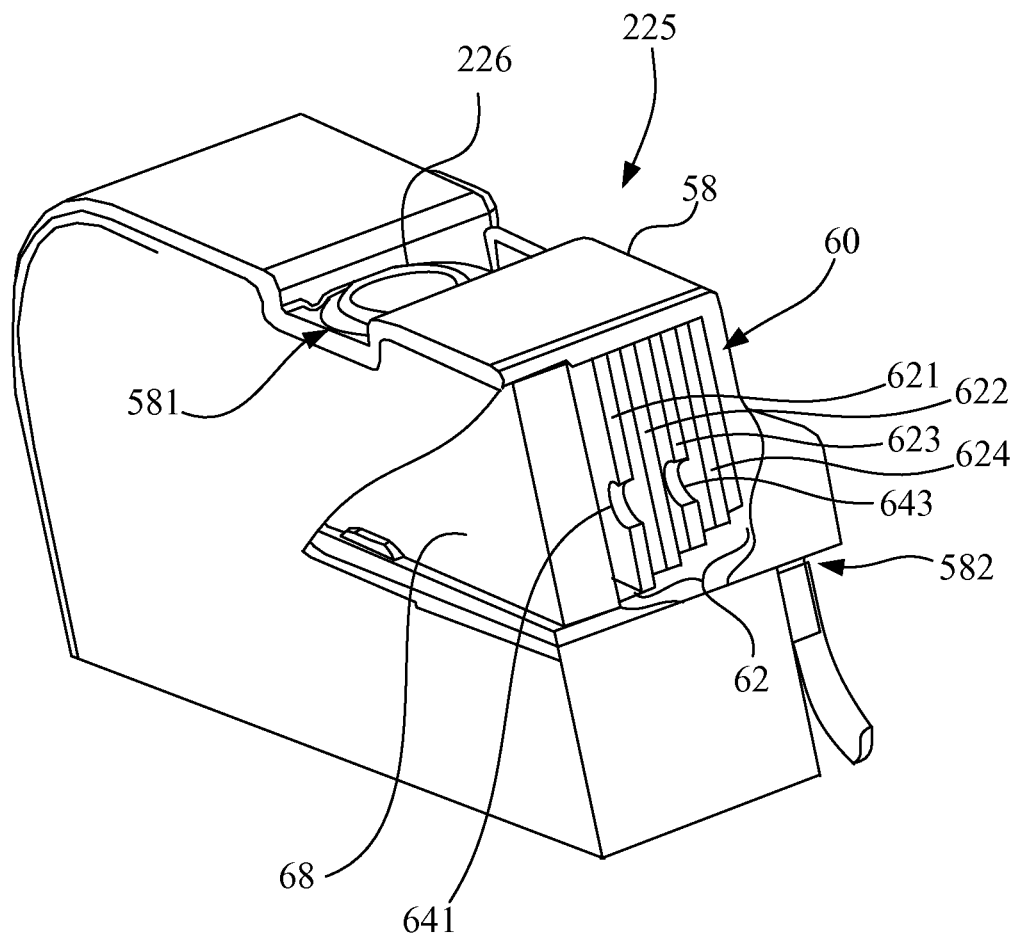
FIG. 5A is a perspective view of the fluid management tank of the disposable biopsy probe shown in FIGS. 2 and 3, with a portion broken away to expose a filter arrangement.

Referring also to FIG. 5A, fluid management tank 225 is fluidically interposed in the second vacuum path 22 between the first end 221 and the second end 222. Fluid management tank 225 includes a body 58 and a filter arrangement 60 contained within body 58 configured to prevent a flow of residual biopsy biological material, e.g., blood and particulate matter, from sample notch 444 of sample basket 441 to vacuum source 18 of driver assembly 12.

Body 58 of fluid management tank 225 has a first port 581 and a second port 582, with the second vacuum path 22 continuing between the first port 581 and the second port 582. The second port 582 of fluid management tank 225 is coupled to sample basket 441. Each of the second one-way valve 224 and the second vacuum seal element 226 of the second vacuum path 22 is coupled to the first port 581 of fluid management tank 225, and in the present embodiment, is mounted to an external surface of body 58 of fluid management tank 225.

Figure 5B:
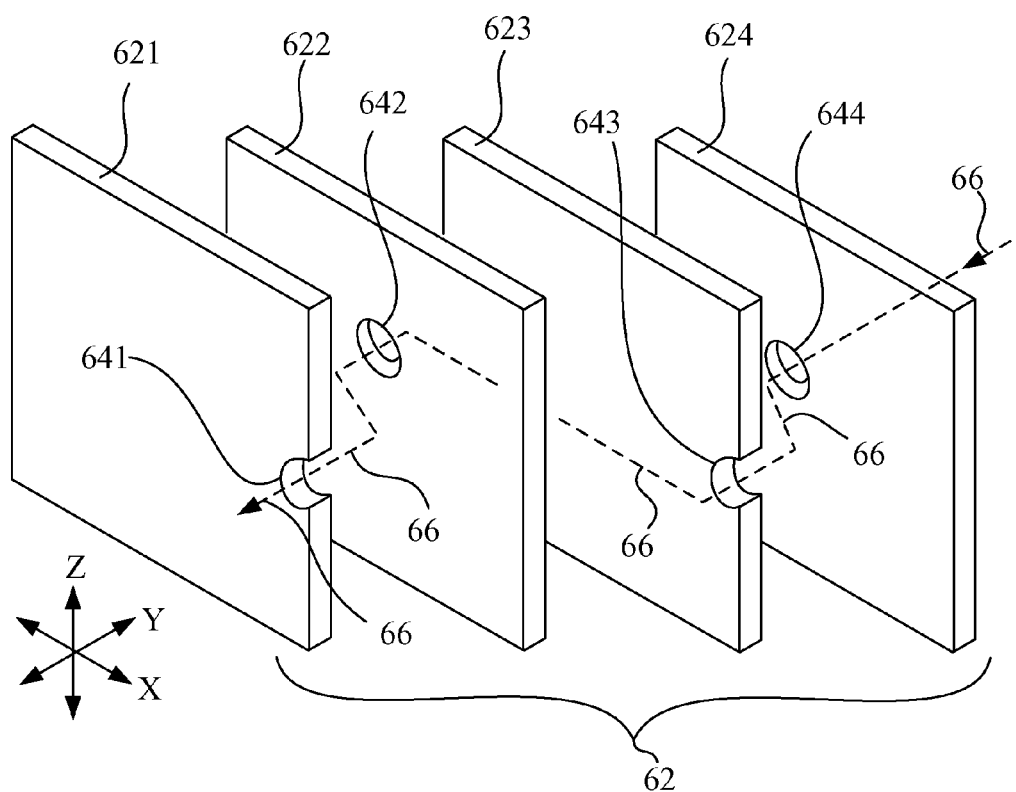
FIG. 5B is an exploded view of a plurality of fluid absorption layers of the filter arrangement of FIG. 5A.

As illustrated in FIGS. 5A and 5B, filter arrangement 60 includes a plurality of fluid absorption layers 62, individually identified as layers 621, 622, 623 and 624, arranged side by side, with each fluid absorption layer 621, 622, 623 and 624 being spaced apart from an adjacent fluid absorption layer e.g., 621 to 622, 622 to 623, 623, to 624. Each fluid absorption layer 621, 622, 623 and 624 has a respective through opening 641, 642, 643, 644, wherein adjacent through openings of through openings 641, 642, 643, 644 of the plurality of fluid absorption layers 62 are offset one to the next, e.g., in at least one of an X, Y, and Z direction, to form a tortuous open fluid passageway 66 through the plurality of fluid absorption layers 62. Each fluid absorption layer 621, 622, 623 and 624 may be, for example, a blotting paper.

Figure 5C:
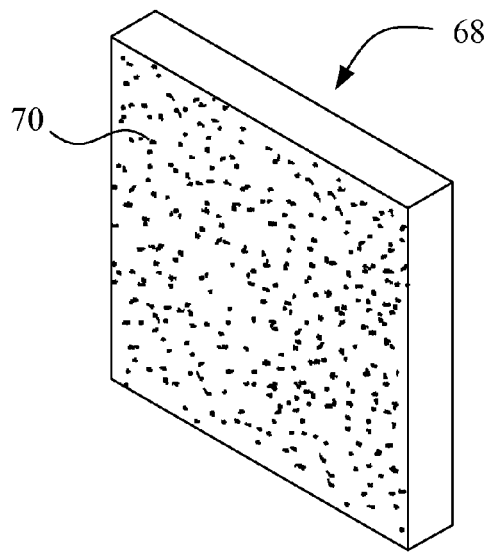
FIG. 5C is a perspective view of a porous filter element of the filter arrangement of FIG. 5A.

As illustrated in FIGS. 5A and 5C, filter arrangement 60 may further include a porous filter element 68 arranged to be fluidically in series with the plurality of fluid absorption layers 62 along the second vacuum path 22 that defines second passageway 227. The porous filter element 68 exhibits increased restriction to fluid flow as an increased number of pores 70 in the porous filter element 68 become clogged by residual biopsy biological material, such as blood and tissue particles. When a volume of the fluid flow through fluid management tank 225 has been reduced to a predetermined level, vacuum monitoring mechanism 30 senses the vacuum restriction, and controller 26 responds to shut off vacuum source 18.

Referring to FIGS. 6-13, each harvested tissue sample is transported out of the body of the patient and is collected by tissue sample retrieval mechanism 56. In general, tissue sample retrieval mechanism 56 collects tissue samples that have been harvested by scooping the tissue sample out of sample notch 444 of sample basket 441 of biopsy probe 44.

Figure 6:
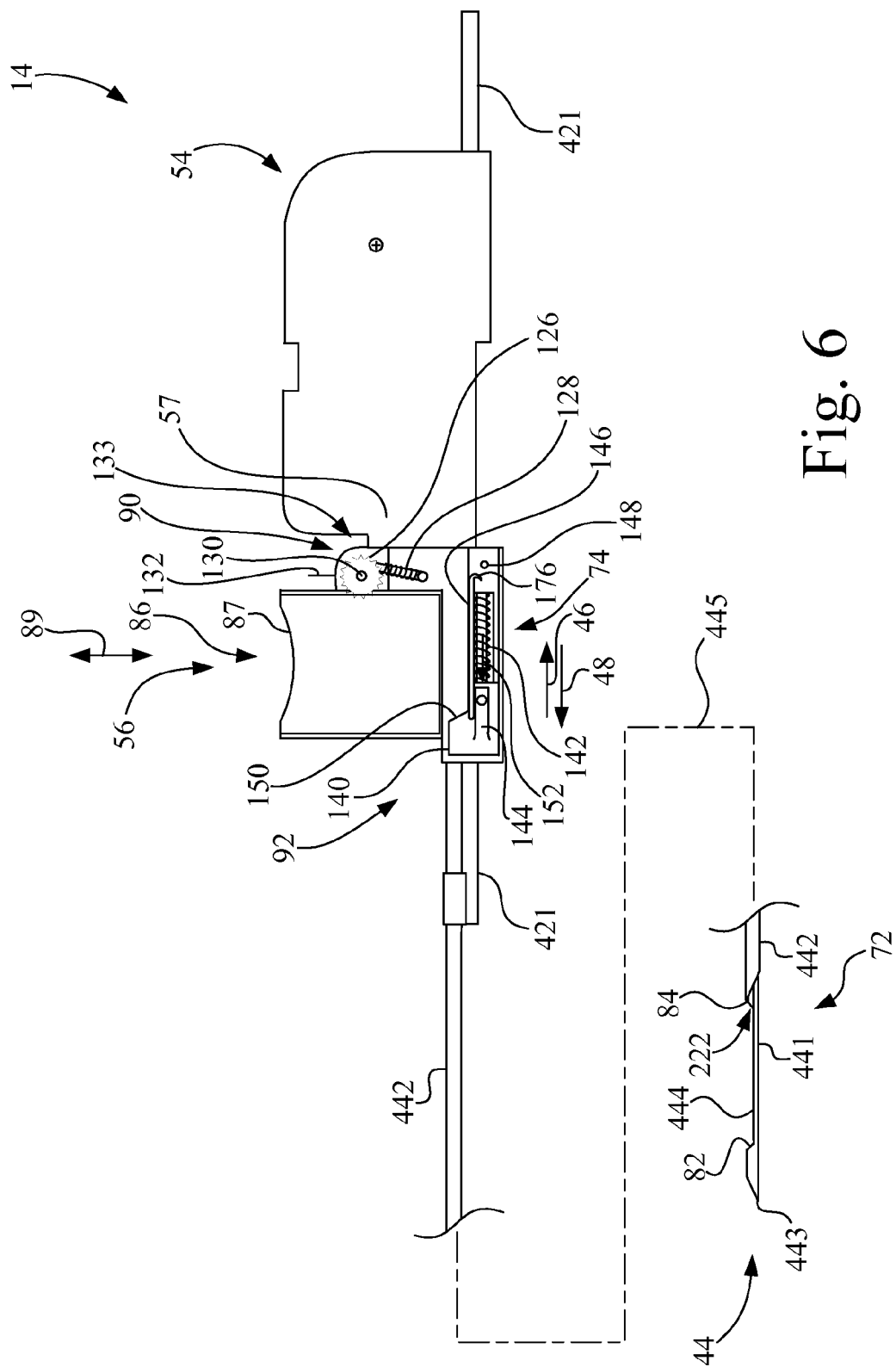
FIG. 6 is a side view of the disposable biopsy probe of FIG. 2 showing in further detail a tissue sample retrieval mechanism with the sample collection tank removed.
Figure 7:
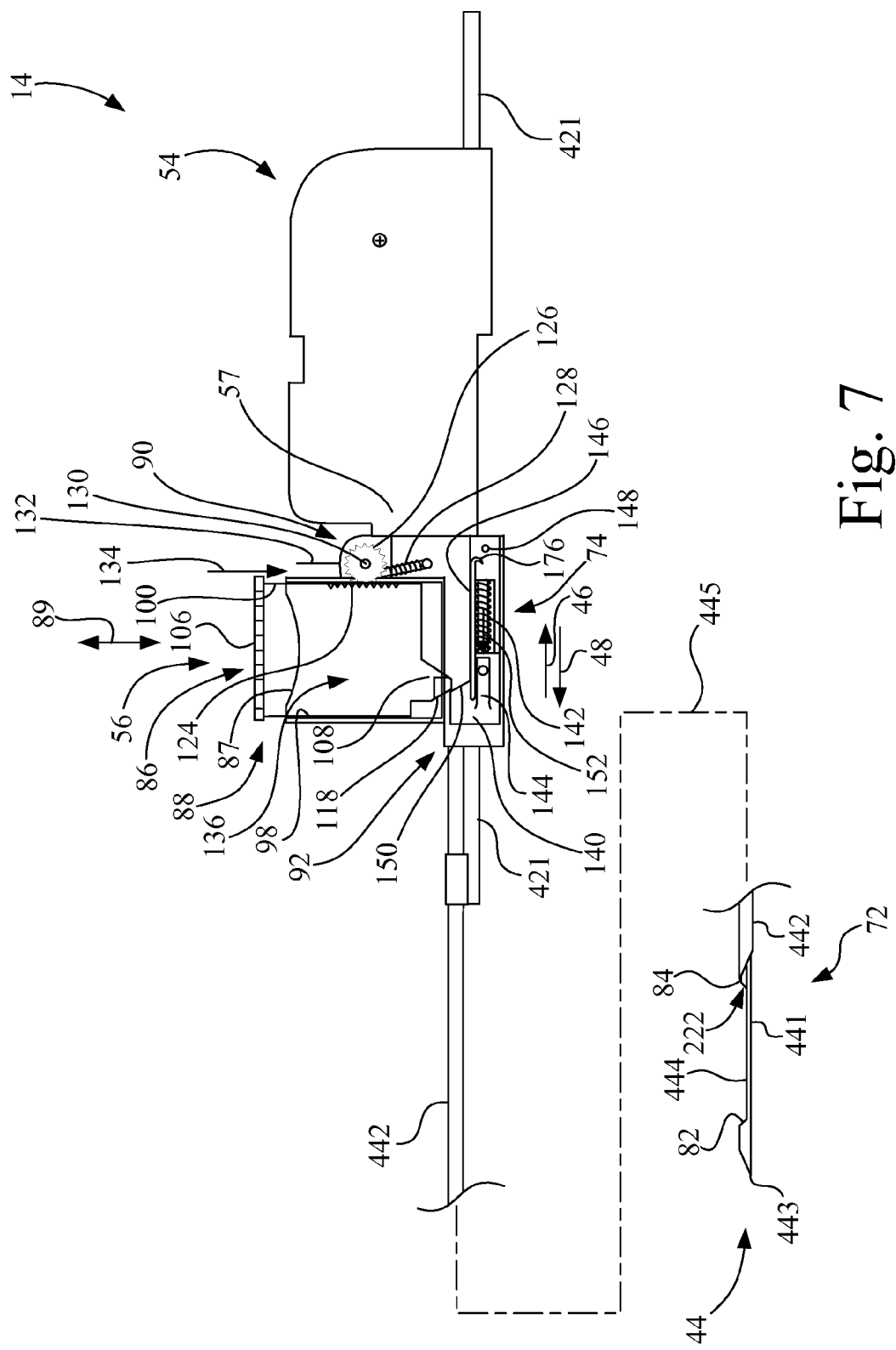
FIG. 7 is a side view of the disposable biopsy probe of FIG. 6 showing the tissue sample retrieval mechanism with the sample collection tank installed, and with the sample collection tank in the raised position.
Figure 8:
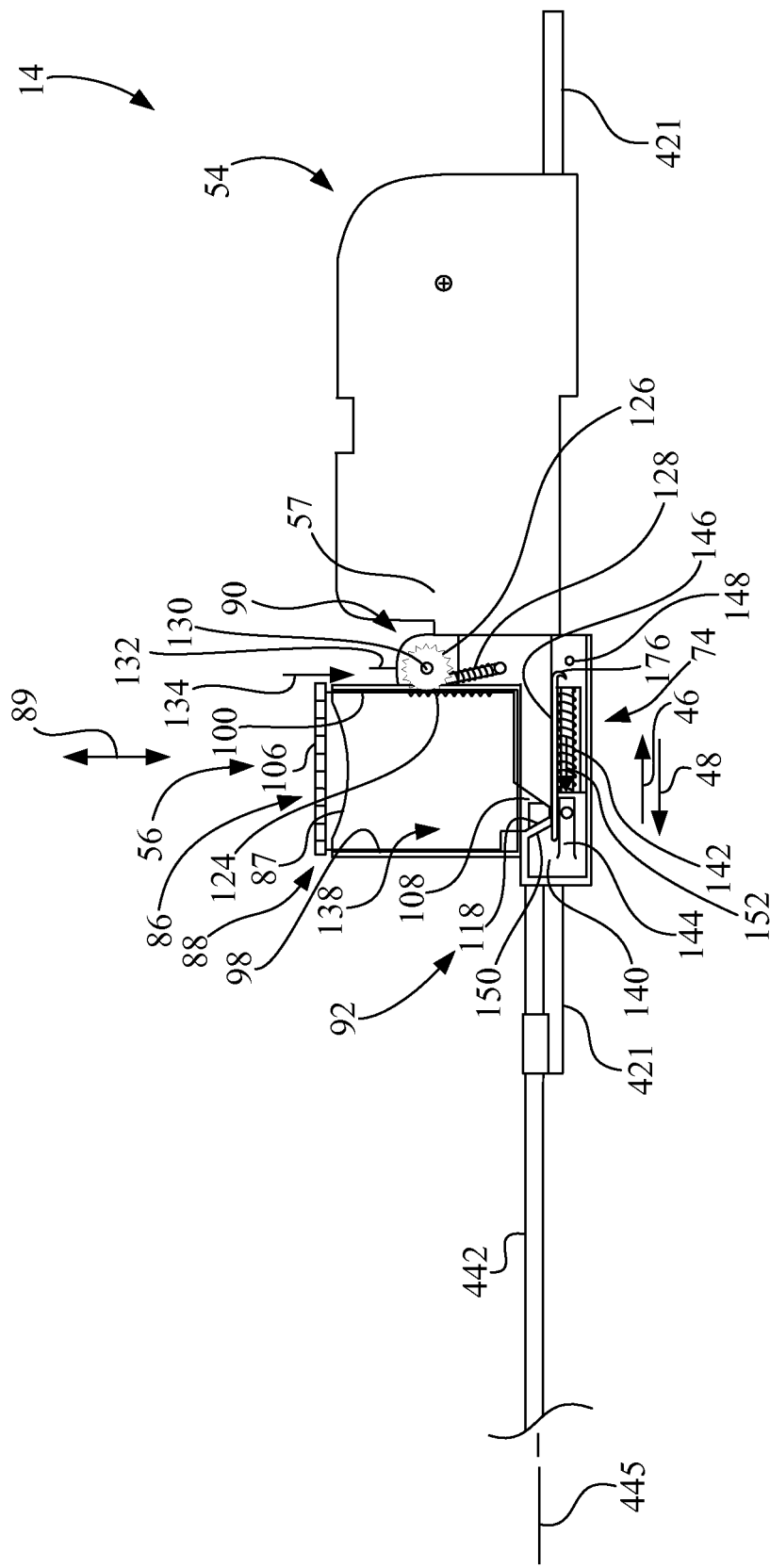
FIG. 8 is a side view of the disposable biopsy probe of FIG. 6 showing the tissue sample retrieval mechanism with the sample collection tank installed, and with the sample collection tank in the lowered collection position.
Figure 12:
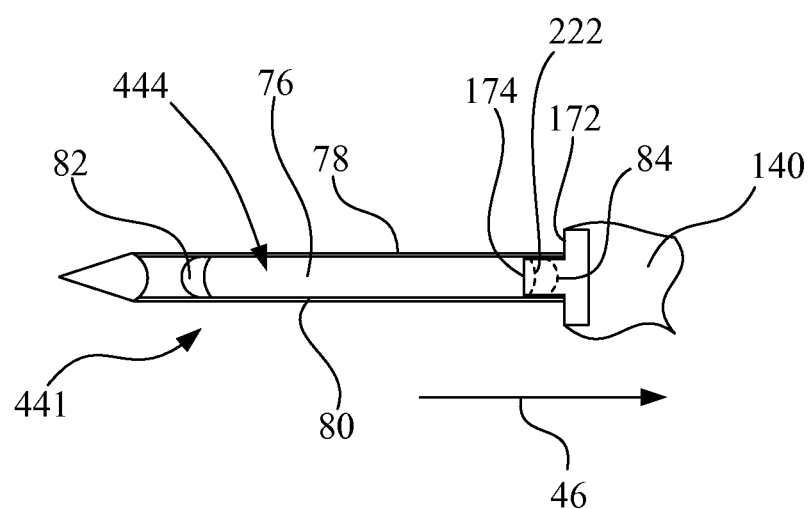
FIG. 12 is a top view of the sample basket and the lift member of the disposable biopsy probe of FIG. 7, with a portion of lift member broken away to expose a T-shaped stop, and a leaf spring tongue forming a portion of the T-shaped stop for removing residual tissue material and debris from a vacuum path at the sample notch of the sample basket.

Referring to FIGS. 6-9, biopsy probe 44 of probe assembly 14 includes a biopsy cannula, e.g., cutter cannula 442, and sample basket 441 arranged coaxially about longitudinal axis 445. Sample basket 441 having sample notch 444 is movably disposed relative to biopsy cannula 442 along longitudinal axis 445 from a tissue harvesting position 72, as shown in FIGS. 6 and 7, to a tissue sample retrieval region 74, as illustrated in FIGS. 6-8 by electromechanical power source 28 and second drive 362, as more fully described above with respect to FIG. 3. Referring also to FIGS. 10 and 12, sample notch 444 is an elongate recessed region of sample basket 441 having a generally semicircular cross-section, and has a recessed floor 76, a pair of spaced elongate edges 78, 80 on opposite sides of recessed floor 76, a leading transition bevel 82, and a trailing transition bevel 84. Leading transition bevel 82 and trailing transition bevel 84 are located at opposite ends of the elongate recessed region, i.e., sample notch, 444.

In the present embodiment, tissue sample retrieval mechanism 56 includes a sample tank receptacle 86, a sample collection tank 88, a toggle mechanism 90, and a tank positioning mechanism 92. Sample collection tank 88 is configured for removable insertion into sample tank receptacle 86.

Sample tank receptacle 86, which may be formed integral with housing 57, includes a hollow guide 87 size to slidably receive sample collection tank 88. Thus, the configuration of sample tank receptacle 86 is such that sample tank receptacle 86 permits bi-directional movement of sample collection tank 88 in directions 89 (signified by double headed arrow) that are substantially perpendicular to longitudinal axis 445. Also, the configuration of sample tank receptacle 86 is such that sample tank receptacle 86 prohibits movement of sample collection tank 88 in a direction 46 or 48 along longitudinal axis 445.

Sample collection tank 88 defines a single collection cavity 94 (see FIG. 9) configured for receiving multiple tissue samples, such as tissue sample TS. Sample collection tank 88 has, in forming collection cavity 94, a base 96, a front wall 98, a rear wall 100, a pair of side walls 102, 104, and a removable cap 106. Sample collection tank 88 further includes a tissue sample scoop 108. Sample collection tank 88 is configured to collect a tissue sample directly from sample notch 444 as sample basket 441 moves along longitudinal axis 445 at tissue sample retrieval region 74. In this regard, tissue sample scoop 108 of sample collection tank 88 is configured to engage sample notch 444 of sample basket 441.

Tissue sample scoop 108 is fixed to and projects downwardly from base 96. Tissue sample scoop 108 extends forward toward a front portion 110 of sample collection tank 88 to terminate at a rim 112. Tissue sample scoop 108 has a tissue collection lumen 114 through which each tissue sample TS harvested by biopsy probe assembly 14 will pass. Tissue collection lumen 114 begins at an opening 116 located near rim 112 and extends to collection cavity 94. Tissue sample scoop 108 has a ramped face 118 located adjacent rim 112. Also, tissue sample scoop 108 has a first shoulder 120 and a second shoulder 122 that are positioned on opposite sides of opening 116.

A rack gear 124 is longitudinally (e.g., vertically) positioned on rear wall 100 of sample collection tank 88 to engage toggle mechanism 90.

Referring to FIGS. 6-9, toggle mechanism 90 is configured to aid in the mounting of sample collection tank 88 in sample tank receptacle 86, and to aid in the removal of sample collection tank 88 from sample tank receptacle 86. Toggle mechanism 90 is mounted to housing 57 and includes a rotary gear 126 and a spring 128. Rotary gear 126 has a rotational axis 130, e.g., an axle, which is attached to, or formed integral with, housing 57. Spring 128 is coupled between rotary gear 126 and housing 57, and is eccentrically mounted to rotary gear 126, i.e., at a location offset from rotational axis 130. Rotary gear 126 is located for driving engagement with rack gear 124 of sample collection tank 88, as sample collection tank 88 is slidably received by sample tank receptacle 86.

Referring to FIGS. 6-8, toggle mechanism 90 is configured to define a break-over point 132, e.g., at the 12:00 o'clock position in the orientation as shown. FIG. 6 shows an orientation of toggle mechanism 90 when sample collection tank 88 is not installed in hollow guide 87 of sample tank receptacle 86, where spring 128 is positioned beyond the 12 o'clock position in a clockwise direction in the orientation as shown, thus defining a home position 133 for toggle mechanism 90.

FIG. 7 shows an orientation of toggle mechanism 90 when sample collection tank 88 is installed (inserted) in hollow guide 87 of sample tank receptacle 86. As sample collection tank 88 is inserted in hollow guide 87 of sample tank receptacle 86, rack gear 124 of sample collection tank 88 engages rotary gear 126 and rotates rotary gear 126 about rotational axis 130 in the counterclockwise direction in the orientation as shown. When spring 128 is moved beyond break-over point 132, e.g., the 12 o'clock position, in the counterclockwise direction as sample collection tank 88 is slidably received by sample tank receptacle 86, spring 128 provides a biasing force 134, e.g., a downward pressure, via rotary gear 126 to bias sample collection tank 88 downwardly toward longitudinal axis 445. Thus, biasing force 134 exerts downward pressure on sample collection tank 88 when spring 128 is moved beyond the 12 o'clock position in the counterclockwise direction, in the orientation as shown in FIG. 7, and biasing force 134 is maintained when sample collection tank 88 is installed in sample tank receptacle 86.

Figure 9:
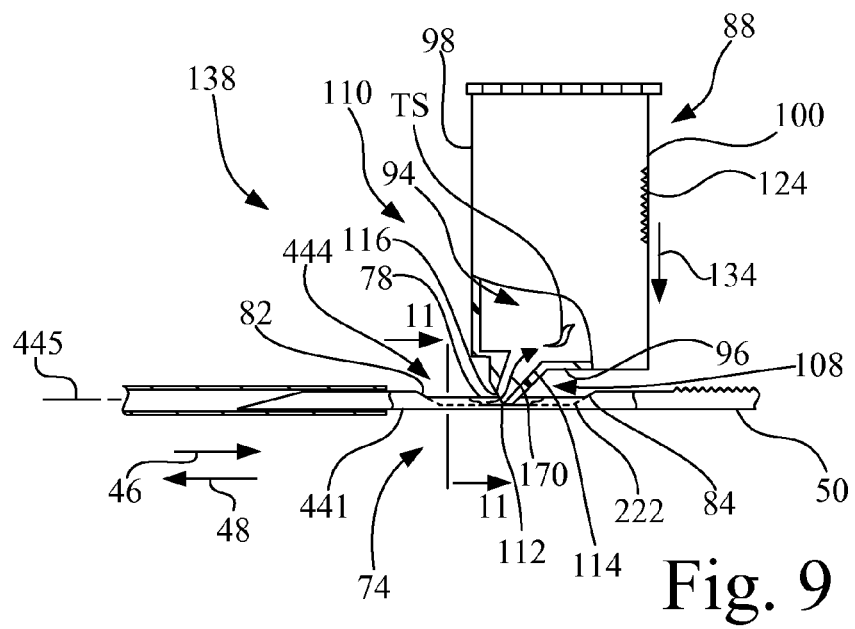
FIG. 9 is a side view of a portion of the tissue sample retrieval mechanism of FIG. 8 with a portion of the cutter cannula sectioned away to expose the retracting sample basket, and with a portion of the sample basket broken way to show the interaction of the scoop of the sample collection tank with the sample notch.
Figure 11:
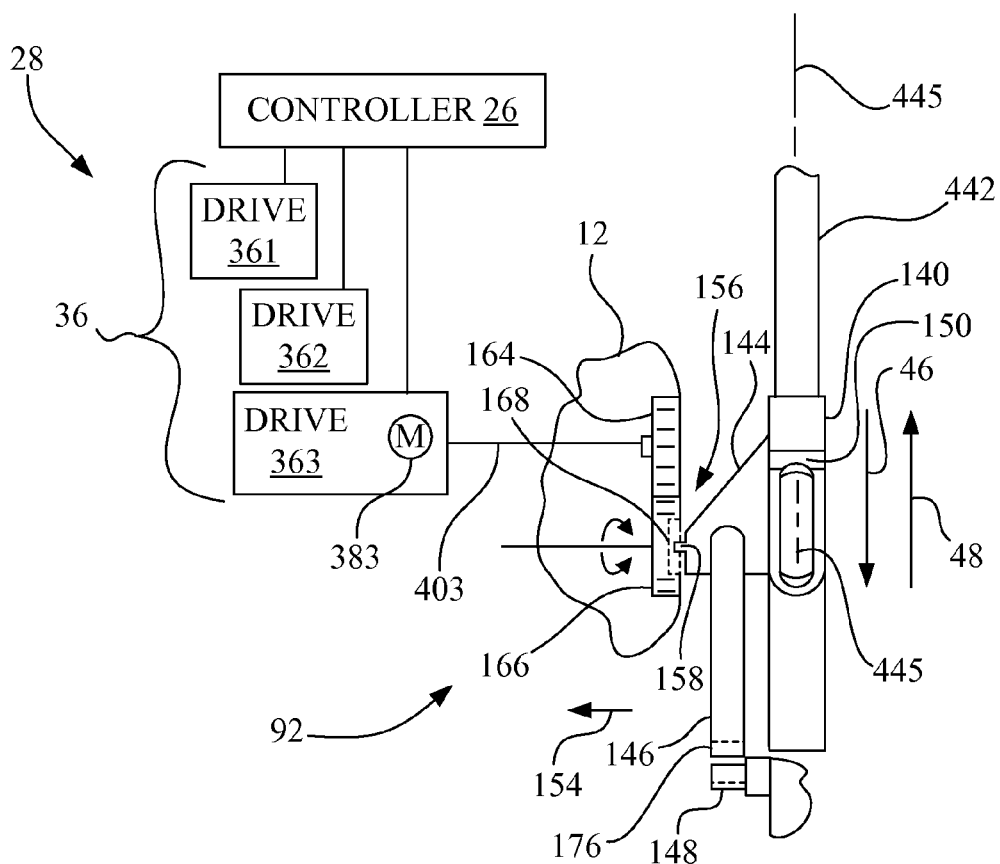
FIG. 11 is a top view of the tank positioning mechanism shown in FIG. 8.
Figure 10:
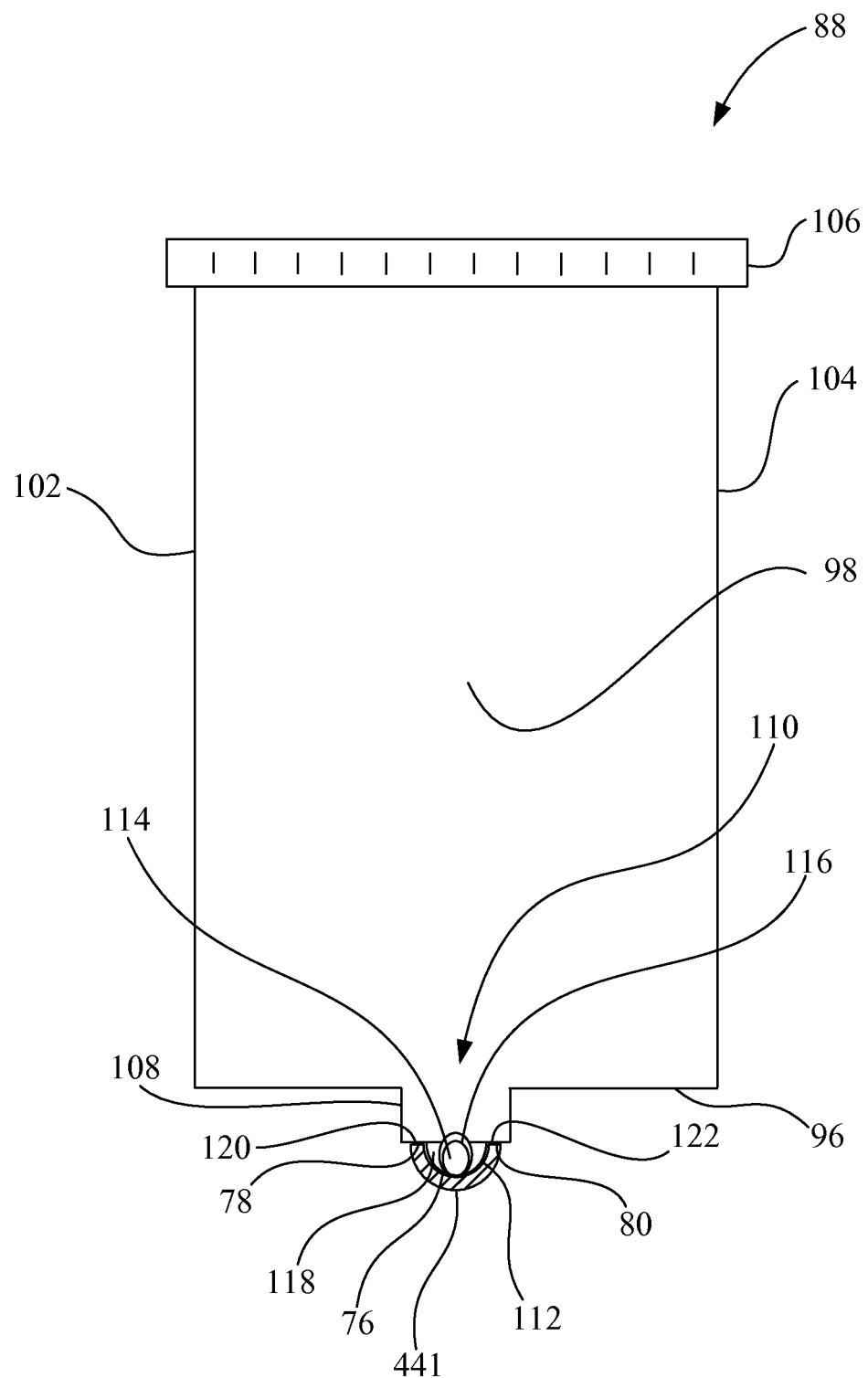
FIG. 10 is an enlarged front view of a portion of the sample collection tank of FIG. 9 showing the interaction of the scoop of the sample collection tank with the sample notch, and with the sample notch being shown in section view taken along line 11-11 of FIG. 9.

Referring to FIG. 11 in conjunction with FIGS. 7-9, tank positioning mechanism 92 is configured to selectively move sample collection tank 88 between a raised position 136 illustrated in FIG. 7 and a lowered position 138 illustrated in FIGS. 8 and 9.

Tank positioning mechanism 92 is drivably engaged with electromechanical power source 28 to selectively lower, in conjunction with toggle mechanism 90, sample collection tank 88 from raised position 136 to lowered position 138 to position a portion, i.e., tissue sample scoop 108, of sample collection tank 88 in sliding engagement with sample notch 444 to facilitate collection of a tissue sample, e.g., tissue sample TS, from sample basket 441 as sample basket 441 is moved in tissue sample retrieval region 74. Also, electromechanical power source 28 is drivably engaged with tank positioning mechanism 92 and/or flexible toothed rack 50 to selectively raise sample collection tank 88, against the biasing force 134 exerted by toggle mechanism 90 and the biasing force 152 exerted by tank positioning mechanism 92, from lowered position 138 to raised position 136 to disengage sample collection tank 88 from sample notch 444 of sample basket 441 prior to, and following, tissue collection from sample basket 441.

More particularly, referring to FIGS. 6-8 and 11, tank positioning mechanism 92 includes a lift member 140, a spring 142, a lever 144, a latch member 146 and a latch catch 148.

Referring to FIGS. 7 and 8, lift member 140 is positioned along longitudinal axis 445. Lift member 140 has a ramp surface 150 positioned to engage ramped face 118 of sample collection tank 88. Spring 142 is positioned between lift member 140 and housing 57 to exert biasing force 152 on lift member 140 to bias ramp surface 150 in a direction away from ramped face 118 of sample collection tank 88.

As shown in FIG. 11, lever 144 extends from lift member 140 in a direction 154 perpendicular to longitudinal axis 445. Lever 144 has a distal end 156 configured to engage electromechanical power source 28, which may be in the form of a pin 158.

Electromechanical power source 28 is operable to move lift member 140 along longitudinal axis 445 in direction 46 to lift sample collection tank 88 away from longitudinal axis 445 as ramp surface 150 of lift member 140 slides along ramped face 118 of sample collection tank 88. Likewise, electromechanical power source 28 is operable to move lift member 140 along longitudinal axis 445 in direction 48 opposite first direction 46 to lower sample collection tank 88 toward longitudinal axis 445 as ramp surface 150 of lift member 140 slides along ramped face 118 of sample collection tank 88.

As shown in FIG. 11, electromechanical power source 28 includes a lift drive 363 having an electrical motor 383 coupled to a motion transfer unit 403 (shown schematically in part by a line) that generally terminates at gears 164 and 166. Gear 166 includes a slot 168 for engaging pin 158 of lever 144. Motion transfer unit 403 provides rotary motion to gear 164, which in turn imparts rotary motion to gear 166. Motion transfer unit 403 may include one or more of a gear, gear train, belt/pulley arrangement, etc., for effecting at least a partial rotation of gear 164. Gear 166, however, is only rotated at a partial revolution, so as to effect a linear translation of pin 158 of lever 144, and in turn a linear translation of lift member 140.

The lowering of sample collection tank 88 for tissue sample collection (retrieval) is initiated by electromechanical power source 28 wherein gear 166 of lift drive 363 of electromechanical power source 28 is rotated in a direction to translate the lever 144, and in turn lift member 140, in direction 48 to lower sample collection tank 88. Biasing force 152 exerted on lift member 140 aids in moving ramp surface 150 in direction 48 away from ramped face 118 of sample collection tank 88. At this time, first shoulder 120 and second shoulder 122 of tissue sample scoop 108 are positioned for respective sliding engagement with the pair of spaced elongate edges 78, 80 of the elongate recessed region of sample notch 444 of sample basket 441 along longitudinal axis 445.

More particularly, with reference to FIGS. 8 and 11, the translation of the lever 144 and in turn lift member 140 in direction 48 causes the oblique face ramped face 118 of sample collection tank 88 to slide down the oblique ramp surface 150 of lift member 140, and tissue sample scoop 108 with rim 112 are moved into the elongate recessed region of sample notch 444 of sample basket 441 toward recessed floor 76. Referring also to FIGS. 9 and 10, continued transport of the sample notch 444 in direction 46 by electromechanical power source 28 will cause rim 112 of tissue sample scoop 108 to slide along recessed floor 76 and along the sides between elongate edges 78, 80 of sample notch 444, scooping up the tissue sample TS and transporting the tissue sample TS through tissue collection lumen 114 into collection cavity 94 of sample collection tank 88 along path 170. The shoulders 120, 122 of sample collection tank 88 are configured to slide along the upper spaced elongate edges 78, 80 of sample basket 441, ensuring that no tissue sample material is pushed out of sample notch 444.

The raising of sample collection tank 88 occurs near the conclusion of the tissue collection sequence. Near the conclusion of the tissue collection sequence, the further movement of sample notch 444 of sample basket 441 in direction 46 by operation of electromechanical power source 28 and second drive 362 is transferred to lift member 140 by a driving engagement of sample basket 441 in direction 46 with a T-shaped stop 172 (see FIG. 12) attached to lift member 140, causing lift member 140 to move in direction 46. The scoop rim 112 of sample collection tank 88 reaches the sloping leading transition bevel 82 of sample notch 444 and is pushed upwards by the interplay between ramped face 118 of sample collection tank 88 and leading transition bevel 82 of sample notch 444, thus beginning to raise sample collection tank 88. As lift member 140 is further moved in direction 46 by movement of sample notch 444, the scoop rim 112 leaves sample notch 444 and ramped face 118 of sample collection tank 88 and comes to rest against ramp surface 150 of lift member 140, which closes off tissue collection lumen 114 of sample collection tank 88 and prevents the tissue sample TS from falling out of tissue collection lumen 114.

In addition, lift drive 363 is rotated to ensure that lift member 140 is translated fully in direction 46 in the event that the force exerted by sample notch 444 is insufficient to accomplish the translation. More particularly, electromechanical power source 28 rotates gear 166 of lift drive 363 in a direction to translate the lever 144 in direction 46. Thus, electromechanical power source 28 facilitates movement of lift member 140 along longitudinal axis 445 in first direction 46 against the biasing force 152 exerted by spring 142 to lift sample collection tank 88 as ramp surface 150 of lift member 140 slides along ramped face 118 of sample collection tank 88.

At the conclusion of the transport of sample notch 444 in direction 46 towards the proximal end of driver assembly 12, a leaf spring tongue 174 of T-shaped stop 172 (see FIG. 12) removes residual tissue material and debris from the second end 222 of vacuum path 22 at trailing transition bevel 84 of sample notch 444 to ensure that a sufficient vacuum may be drawn into sample notch 444.

Referring again to FIGS. 6-8, 11 and 13, latch member 146 is attached to, or formed integral with, lift member 140. Latch member 146 extends from lever 144 in direction 46, and has a distal hook 176. Latch member 146 is located for engagement with latch catch 148 to latch lift member 140 in a transport latched position, shown in FIG. 13, corresponding to raised position 136 of sample collection tank 88. Latch catch 148 may be attached to, or formed integral with, housing 57.

Figure 13:
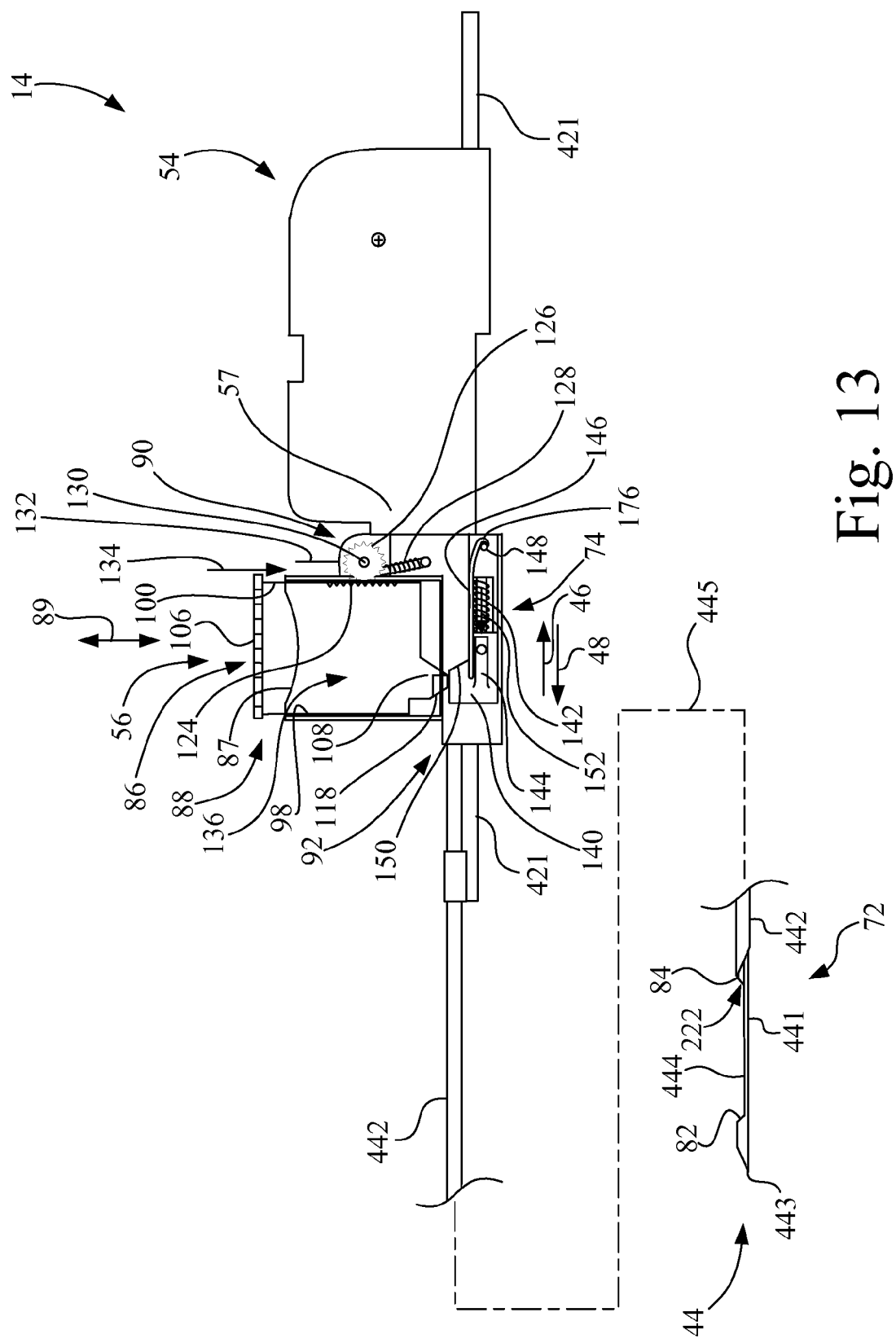
FIG. 13 is a side view of the disposable biopsy probe of FIG. 7 showing the latch member of the tank positioning mechanism in the latched transport position.

One purpose of latch member 146 is to maintain the proper insertion position of lever 144 during transport of biopsy probe assembly 14 to ensure proper insertion of biopsy probe assembly 14 in driver assembly 12. Prior to insertion of biopsy probe assembly 14 in driver assembly 12, lever 144 is held in a latched transport position, which is the only position permitting pin 158 at distal end 156 of lever 144 to be inserted into slot 168 (e.g., a driver recess) of lift drive 363 (see FIG. 11). In the latched transport position, as illustrated in FIG. 13, the lever 144 is held in position by latch member 146 that is held in tension against latch catch 148 by pressure (biasing force 152) from spring 142. Thus, insertion of biopsy probe assembly 14 in driver assembly 12 in the latched transport position results in placement of pin 158 at distal end 156 of lever 144 in slot 168 (e.g., a driver recess) of lift drive 363.

A second purpose of the latch member 146 is to prevent accidental reuse of the disposable probe. As part of power up, the lift drive 363 engages pin 158 at distal end 156 of lever 144 and moves lever 144 in direction 46 to a fully retracted position, which in turn causes latch member 146 to move out of engagement with latch catch 148. The tension of the latch member 146 is released, causing latch member 146 to move out of the plane of latch catch 148 and preventing latch member 146 from reestablishing contact with latch catch 148. Since spring 142 will bias lift member 140 in direction 48, the latched transport position illustrated in FIG. 13 may not be reestablished once biopsy probe assembly 14 has been removed from driver assembly 12. Since the latched transport position is the only position permitting biopsy probe assembly 14 to be inserted in driver assembly 12, accidental reuse of biopsy probe assembly 14 is prevented.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy apparatus, comprising:
an electromechanical power source;
a biopsy probe drivably coupled to said electromechanical power source, said biopsy probe including a biopsy cannula and a sample basket arranged coaxially about a longitudinal axis, said sample basket being movably disposed relative to said biopsy cannula along said longitudinal axis from a tissue harvesting position to a tissue sample retrieval region, said sample basket having a sample notch configured as an elongate recessed region for receiving a tissue sample; and
a tissue sample retrieval mechanism including a sample tank receptacle and a sample collection tank configured for removable insertion into said sample tank receptacle, said sample tank receptacle being configured to permit movement of said sample collection tank in a direction perpendicular to said longitudinal axis and being configured to prohibit movement of said sample collection tank in a direction along said longitudinal axis, said sample collection tank being configured to retrieve said tissue sample directly from said sample notch as said sample basket is moving along said longitudinal axis at said tissue sample retrieval region.

2. The biopsy apparatus of claim 1, wherein said tissue sample retrieval mechanism includes a tank positioning mechanism configured to selectively move said sample collection tank between a raised position and a lowered position, said tank positioning mechanism being drivably coupled to said electromechanical power source and configured to selectively lower said sample collection tank from said raised position to said lowered position to position a sample notch engaging portion of said sample collection tank in sliding engagement with said sample notch to facilitate retrieval of a tissue sample from said sample basket as said sample basket is moved in said tissue sample retrieval region.

3. The biopsy apparatus of claim 1, wherein said sample collection tank defines a single collection cavity configured for receiving multiple tissue samples, said sample collection tank having a base and a tissue sample scoop configured to engage said sample notch of said sample basket, said tissue sample scoop fixedly projecting downwardly from said base and extending forward toward a front of said sample collection tank to terminate at a rim, said tissue sample scoop having a tissue collection lumen that extends from an opening to said collection cavity.

4. The biopsy apparatus of claim 3, wherein said a tissue sample retrieval mechanism includes a tank positioning mechanism configured to selectively move said sample collection tank in said sample tank receptacle between a raised position and a lowered position, said tank positioning mechanism being drivably engaged with said electromechanical power source and configured to selectively lower said sample collection tank from said raised position to said lowered position to position said tissue sample scoop in sliding engagement with said sample notch to facilitate retrieval of a tissue sample from said sample basket as said sample basket is moved in said tissue sample retrieval region.

5. The biopsy apparatus of claim 4, wherein said sample collection tank has a ramped face, said tank positioning mechanism including:
   a lift member positioned along said longitudinal axis, said lift member having a ramp surface positioned to engage said ramped face of said sample collection tank, said lift member being configured and arranged for drivable coupling to said electromechanical power source,
      said electromechanical power source being operable to move said lift member along said longitudinal axis in a first direction to lift said sample collection tank away from said longitudinal axis as said ramp surface of said lift member slides along said ramped face of said sample collection tank, and
      said electromechanical power source being operable to move said lift member along said longitudinal axis in a second direction opposite said first direction to lower said sample collection tank toward said longitudinal axis as said ramp surface of said lift member slides along said ramped face of said sample collection tank.

6. The biopsy apparatus of claim 5, wherein said sample tank receptacle is integral with a housing, said housing having a latch catch, and further including a lever extending from said lift member, and a latch member being configured to extend from said lever in said first direction, said latch member being located for engagement with said latch catch to latch said lift member in a latched transport position corresponding to said raised position of said sample collection tank.

7. The biopsy apparatus of claim 5, wherein said ramped face is located at said scoop of said sample collection tank adjacent said rim.

8. The biopsy apparatus of claim 3, wherein said elongate recessed region of said sample notch has a pair of spaced elongate edges, and said tissue sample scoop has a first shoulder and a second shoulder that are positioned on opposite sides of said opening and configured for sliding engagement with said pair of spaced elongate edges of said elongate recessed region along said longitudinal axis, with said rim of said tissue sample scoop being configured to be positioned in said elongate recessed region during retrieval of said tissue sample from said sample notch.

9. The biopsy apparatus of claim 1, wherein said sample collection tank has a rear wall and a rack gear longitudinally positioned on said rear wall, said biopsy apparatus further including a toggle mechanism including a rotary gear having a rotational axis and a first spring coupled to said rotary gear at a location offset from said rotational axis, said rotary gear being located for driving engagement with said rack gear as said sample collection tank is slidably received by said sample tank receptacle, said toggle mechanism being configured to define a break-over point where said first spring provides a first biasing force via said rotary gear to bias said sample collection tank toward said longitudinal axis when said sample collection tank is installed in said sample tank receptacle.

10. The biopsy apparatus of claim 9, wherein said sample collection tank has a ramped face, and said tissue sample retrieval mechanism including:
   a lift member positioned along said longitudinal axis, said lift member having a ramp surface positioned to engage said ramped face of said sample collection tank;
   a second spring positioned to exert a second biasing force on said lift member to bias said ramp surface in a direction away from said ramped face; and
   a lever extending from said lift member, said lever having a distal end configured to engage said electromechanical power source to facilitate movement of said lift member along said longitudinal axis in a direction against said second biasing force exerted by said second spring to lift said sample collection tank as said ramp surface of said lift member slides along said ramped face of said sample collection tank.

11. A biopsy apparatus, comprising:
   a driver assembly configured to be grasped by a user, and having an electromechanical power source; and
   a disposable biopsy probe assembly configured for releasable attachment to said driver assembly, including:
      a transmission device configured for driving engagement with said electromechanical power source;
      a biopsy probe drivably coupled to said transmission device, said biopsy probe including a biopsy cannula and a sample basket arranged coaxially about a longitudinal axis, said sample basket being movably disposed relative to said biopsy cannula along said longitudinal axis from a tissue harvesting position to a tissue sample retrieval region, said sample basket having a sample notch configured as an elongate recessed region for receiving a tissue sample; and
      a tissue sample retrieval mechanism including a sample tank receptacle and a sample collection tank configured for removable insertion into said sample tank receptacle, said sample tank receptacle being configured to permit movement of said sample collection tank in a direction perpendicular to said longitudinal axis and being configured to prohibit movement of said sample collection tank in a direction along said longitudinal axis, said sample collection tank being configured to retrieve said tissue sample directly from said sample notch as said sample basket is moving along said longitudinal axis at said tissue sample retrieval region.

12. The biopsy apparatus of claim 11, wherein said tissue sample retrieval mechanism includes a tank positioning mechanism configured to selectively move said sample collection tank between a raised position and a lowered position, said tank positioning mechanism being drivably coupled to said electromechanical power source and configured to selectively lower said sample collection tank from said raised position to said lowered position to position a sample notch engaging portion of said sample collection tank in sliding engagement with said sample notch to facilitate retrieval of a tissue sample from said sample basket as said sample basket is moved in said tissue sample retrieval region.

13. The biopsy apparatus of claim 11, wherein said sample collection tank defines a single collection cavity configured for receiving multiple tissue samples, said sample collection tank having a base and a tissue sample scoop configured to engage said sample notch of said sample basket, said tissue sample scoop fixedly projecting downwardly from said base and extending forward toward a front of said sample collection tank to terminate at a rim, said tissue sample scoop having a tissue collection lumen that extends from an opening to said collection cavity.

14. The biopsy apparatus of claim 13, wherein said a tissue sample retrieval mechanism includes a tank positioning mechanism configured to selectively move said sample collection tank in said sample tank receptacle between a raised position and a lowered position, said tank positioning mechanism being drivably engaged with said electromechanical power source and configured to selectively lower said sample collection tank from said raised position to said lowered position to position said tissue sample scoop in sliding engagement with said sample notch to facilitate retrieval of a tissue sample from said sample basket as said sample basket is moved in said tissue sample retrieval region.

15. The biopsy apparatus of claim 14, wherein said sample collection tank has a ramped face, said tank positioning mechanism including:
   a lift member positioned along said longitudinal axis, said lift member having a ramp surface positioned to engage said ramped face of said sample collection tank, said lift member being configured and arranged for drivable coupling to said electromechanical power source,
      said electromechanical power source being operable to move said lift member along said longitudinal axis in a first direction to lift said sample collection tank away from said longitudinal axis as said ramp surface of said lift member slides along said ramped face of said sample collection tank, and
      said electromechanical power source being operable to move said lift member along said longitudinal axis in a second direction opposite said first direction to lower said sample collection tank toward said longitudinal axis as said ramp surface of said lift member slides along said ramped face of said sample collection tank.

16. The biopsy apparatus of claim 15, wherein said sample tank receptacle is integral with a housing, said housing having a latch catch, and further including a lever extending from said lift member, and a latch member being configured to extend from said lever in said first direction, said latch member being located for engagement with said latch catch to latch said lift member in a latched transport position corresponding to said raised position of said sample collection tank.

17. The biopsy apparatus of claim 15, wherein said ramped face is located at said scoop of said sample collection tank adjacent said rim.

18. The biopsy apparatus of claim 13, wherein said elongate recessed region of said sample notch has a pair of spaced elongate edges, and said tissue sample scoop has a first shoulder and a second shoulder that are positioned on opposite sides of said opening and configured for sliding engagement with said pair of spaced elongate edges of said elongate recessed region along said longitudinal axis, with said rim of said tissue sample scoop being positioned in said elongate recessed region during retrieval of said tissue sample from said sample notch.

19. The biopsy apparatus of claim 11, wherein said sample collection tank has a rear wall and a rack gear longitudinally positioned on said rear wall, said biopsy apparatus further including a toggle mechanism including a rotary gear having a rotational axis and a first spring coupled to said rotary gear at a location offset from said rotational axis, said rotary gear being located for driving engagement with said rack gear as said sample collection tank is slidably received by said sample tank receptacle, said toggle mechanism being configured to define a break-over point where said first spring provides a first biasing force via said rotary gear to bias said sample collection tank toward said longitudinal axis when said sample collection tank is installed in said sample tank receptacle.

20. The biopsy apparatus of claim 19, wherein said sample collection tank has a ramped face, and said tissue sample retrieval mechanism including:
   a lift member positioned along said longitudinal axis, said lift member having a ramp surface positioned to engage said ramped face of said sample collection tank;
   a second spring positioned to exert a second biasing force on said lift member to bias said ramp surface in a direction away from said ramped face; and
   a lever extending from said lift member, said lever having a distal end configured to engage said electromechanical power source to facilitate movement of said lift member along said longitudinal axis in a direction against said second biasing force exerted by said second spring to lift said sample collection tank as said ramp surface of said lift member slides along said ramped face of said sample collection tank.

* * * * *